US009668768B2

(12) United States Patent
Piron et al.

(10) Patent No.: US 9,668,768 B2
(45) Date of Patent: Jun. 6, 2017

(54) INTELLIGENT POSITIONING SYSTEM AND METHODS THEREFORE

(71) Applicants: Cameron Piron, Toronto (CA); Michael Wood, Toronto (CA); Gal Sela, Toronto (CA); Joshua Richmond, Toronto (CA); Murugathas Yuwaraj, Markham (CA); Stephen McFadyen, Toronto (CA); Alex Panther, Toronto (CA); Nishanthan Shanmugaratnam, Scarborough (CA); William Lau, Toronto (CA); Monroe M. Thomas, Toronto (CA); Wes Hodges, London (CA); Simon Alexander, Toronto (CA); David Gallop, Toronto (CA)

(72) Inventors: Cameron Piron, Toronto (CA); Michael Wood, Toronto (CA); Gal Sela, Toronto (CA); Joshua Richmond, Toronto (CA); Murugathas Yuwaraj, Markham (CA); Stephen McFadyen, Toronto (CA); Alex Panther, Toronto (CA); Nishanthan Shanmugaratnam, Scarborough (CA); William Lau, Toronto (CA); Monroe M. Thomas, Toronto (CA); Wes Hodges, London (CA); Simon Alexander, Toronto (CA); David Gallop, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 14/655,872

(22) PCT Filed: Mar. 14, 2014

(86) PCT No.: PCT/CA2014/050271
§ 371 (c)(1),
(2) Date: Jun. 26, 2015

(87) PCT Pub. No.: WO2014/139023
PCT Pub. Date: Sep. 18, 2014

(65) Prior Publication Data
US 2016/0113728 A1  Apr. 28, 2016

Related U.S. Application Data

(60) Provisional application No. 61/801,530, filed on Mar. 15, 2013, provisional application No. 61/801,746, (Continued)

(51) Int. Cl.
*A61B 17/34* (2006.01)
*A61B 34/20* (2016.01)
(Continued)

(52) U.S. Cl.
CPC .......... *A61B 17/3421* (2013.01); *A61B 34/20* (2016.02); *A61B 34/30* (2016.02);
(Continued)

(58) Field of Classification Search
CPC ...... A61B 17/3421; A61B 2017/00203; A61B 2017/00207; A61B 2034/107; A61B 2034/2051
See application file for complete search history.

(56) References Cited

U.S. PATENT DOCUMENTS 4,609,814 A   9/1986  Nobuaki et al.
5,230,338 A   7/1993  Allen et al.
(Continued)

FOREIGN PATENT DOCUMENTS

DE   102004049258 A1   4/2006
EP       947287 B1     9/2010
(Continued)

OTHER PUBLICATIONS

Choi, Dong-Geol, Byung-Ju Yi, and Whee-kuk Kim. "Automation of Surgical Illumination System Using Robot and Ultrasonic Sensor." Mechatronics and Automation, 2007. ICMA 2007. International Conference on. IEEE, 2007.
(Continued)

*Primary Examiner* — Baisakhi Roy
(74) *Attorney, Agent, or Firm* — Lynn C. Schumacher; Stephen W. Leonard; Hill & Schumacher

(57) ABSTRACT

System and methods are provided for adaptively and interoperatively configuring an automated arm used during a medical procedure. The automated arm is configured to position and orient an end effector on the automated arm a desired distance and orientation from a target. The end effector may be an external video scope and the target may be a surgical port. The positions and orientations of the end effector and the target may be continuously updated. The position of the arm may be moved to new locations responsive to user commands. The automated arm may include a multi-joint arm attached to a weighted frame. The weighted frame may include a tower and a supporting beam.

20 Claims, 31 Drawing Sheets

Related U.S. Application Data filed on Mar. 15, 2013, provisional application No. 61/801,143, filed on Mar. 15, 2013, provisional application No. 61/800,155, filed on Mar. 15, 2013, provisional application No. 61/800,695, filed on Mar. 15, 2013, provisional application No. 61/818,325, filed on May 1, 2013, provisional application No. 61/818,255, filed on May 1, 2013, provisional application No. 61/818,280, filed on May 1, 2013, provisional application No. 61/818,223, filed on May 1, 2013, provisional application No. 61/924,993, filed on Jan. 8, 2014.

(51) Int. Cl.
  *A61B 34/30* (2016.01)
  *A61B 34/10* (2016.01)
  *A61B 17/00* (2006.01)
  *A61B 90/00* (2016.01)
  *A61B 90/50* (2016.01)

(52) U.S. Cl.
  CPC ........... *A61B 2017/00203* (2013.01); *A61B 2017/00207* (2013.01); *A61B 2034/107* (2016.02); *A61B 2034/2051* (2016.02); *A61B 2034/2055* (2016.02); *A61B 2090/3735* (2016.02); *A61B 2090/3983* (2016.02); *A61B 2090/504* (2016.02); *G05B 2219/45123* (2013.01)

(56) References Cited

U.S. PATENT DOCUMENTS

| | | | |
|---|---|---|---|
| 5,445,166 A | 8/1995 | Taylor et al. | |
| 5,630,431 A | 5/1997 | Taylor et al. | |
| 5,696,837 A | 12/1997 | Green et al. | |
| 5,792,147 A | 8/1998 | Evans et al. | |
| 5,876,325 A * | 3/1999 | Mizuno | A61B 1/00048 600/102 |
| 5,907,664 A | 5/1999 | Wang et al. | |
| 6,006,127 A | 12/1999 | Van Der Brug et al. | |
| 6,135,946 A | 10/2000 | Konen et al. | |
| 6,351,659 B1 | 2/2002 | Vilsmeier | |
| 6,441,577 B2 | 8/2002 | Blumenkranz et al. | |
| 6,468,265 B1 | 10/2002 | Evans et al. | |
| 6,519,359 B1 * | 2/2003 | Nafis | G06T 17/00 348/46 |
| 6,546,279 B1 | 4/2003 | Bova et al. | |
| 6,663,559 B2 | 12/2003 | Hale et al. | |
| 6,710,320 B2 * | 3/2004 | Kurata | G01D 5/342 250/208.1 |
| 6,804,581 B2 | 10/2004 | Wang et al. | |
| 6,919,867 B2 | 7/2005 | Sauer | |
| 6,933,695 B2 | 8/2005 | Blumenkranz | |
| 7,491,198 B2 | 2/2009 | Kockro | |
| 7,607,440 B2 | 10/2009 | Coste-Maniere et al. | |
| 7,892,165 B2 | 2/2011 | Nakamura | |
| 7,892,224 B2 | 2/2011 | Hartlep et al. | |
| 8,010,181 B2 | 8/2011 | Smith et al. | |
| 8,073,528 B2 | 12/2011 | Zhao et al. | |
| 8,335,557 B2 | 12/2012 | Maschke | |
| 8,396,598 B2 | 3/2013 | Sutherland et al. | |
| 8,398,541 B2 | 3/2013 | DiMaio et al. | |
| 8,400,094 B2 | 3/2013 | Schena | |
| 8,414,475 B2 | 4/2013 | Sholev | |
| 8,439,830 B2 | 5/2013 | McKinley et al. | |
| 8,571,710 B2 | 10/2013 | Coste-Maniere et al. | |
| 8,624,537 B2 | 1/2014 | Nowlin et al. | |
| 2004/0010190 A1 | 1/2004 | Shahidi | |
| 2004/0015053 A1 | 1/2004 | Bieger et al. | |
| 2004/0210105 A1 | 10/2004 | Hale et al. | |
| 2005/0054895 A1 | 3/2005 | Hoeg et al. | |
| 2005/0096502 A1 * | 5/2005 | Khalili | A61B 1/018 600/106 |
| 2005/0281385 A1 | 12/2005 | Johnson et al. | |
| 2007/0088245 A1 * | 4/2007 | Babaev | A61H 23/0245 604/22 |
| 2008/0109026 A1 | 5/2008 | Kassam | |
| 2008/0201016 A1 | 8/2008 | Finlay | |
| 2008/0243142 A1 | 10/2008 | Gildenberg | |
| 2008/0262297 A1 | 10/2008 | Gilboa et al. | |
| 2009/0043248 A1 * | 2/2009 | Peterson | A61B 17/20 604/22 |
| 2009/0048622 A1 | 2/2009 | Wilson | |
| 2009/0245600 A1 | 10/2009 | Hoffman et al. | |
| 2010/0094085 A1 | 4/2010 | Yamamoto et al. | |
| 2010/0135534 A1 * | 6/2010 | Weston | G01B 11/007 382/106 |
| 2010/0168518 A1 | 7/2010 | De Mathelin et al. | |
| 2010/0198402 A1 * | 8/2010 | Greer | A61B 19/201 700/247 |
| 2011/0162476 A1 | 7/2011 | Nakamura et al. | |
| 2012/0066887 A1 | 3/2012 | Garris et al. | |
| 2012/0071748 A1 | 3/2012 | Mark et al. | |
| 2012/0083661 A1 | 4/2012 | Rockrohr | |
| 2012/0147359 A9 | 6/2012 | Stetten et al. | |
| 2012/0253375 A1 | 10/2012 | Mark et al. | |
| 2012/0265023 A1 | 10/2012 | Berci et al. | |
| 2012/0265060 A1 | 10/2012 | Ramraj et al. | |
| 2012/0265071 A1 | 10/2012 | Berke | |
| 2012/0289816 A1 | 11/2012 | Mark et al. | |
| 2012/0296198 A1 | 11/2012 | Robinson et al. | |
| 2013/0053648 A1 | 2/2013 | Abovitz et al. | |
| 2013/0053866 A1 * | 2/2013 | Leung | B25J 9/1689 606/130 |
| 2013/0066335 A1 | 3/2013 | Barwinkel et al. | |
| 2013/0094742 A1 | 4/2013 | Feilkas | |
| 2013/0102851 A1 | 4/2013 | Mark et al. | |
| 2013/0102886 A1 | 4/2013 | Mark et al. | |
| 2013/0144307 A1 | 6/2013 | Jeong et al. | |
| 2013/0158565 A1 * | 6/2013 | Anvari | A61B 10/0266 606/130 |
| 2013/0204095 A1 | 8/2013 | Mark et al. | |
| 2013/0204287 A1 | 8/2013 | Mark et al. | |
| 2013/0303883 A1 | 11/2013 | Zehavi et al. | |
| 2014/0171873 A1 | 6/2014 | Mark | |
| 2014/0357953 A1 * | 12/2014 | Roelle | A61B 1/00006 600/118 |

FOREIGN PATENT DOCUMENTS

| | | |
|---|---|---|
| EP | 1599148 B1 | 4/2011 |
| EP | 2567668 A1 | 3/2013 |

(56) References Cited

FOREIGN PATENT DOCUMENTS

| WO | 2006095027 A1 | 9/2006 |
|---|---|---|
| WO | 2008115566 A2 | 9/2008 |
| WO | 2011058530 A1 | 5/2011 |
| WO | 2011149187 A2 | 12/2011 |
| WO | 2011156733 A2 | 12/2011 |
| WO | 2012098485 A1 | 7/2012 |

OTHER PUBLICATIONS

Lee, Cheolwhan, et al. "Image analysis for automated tracking in robot-assisted endoscopic surgery." Pattern Recognition, 1994. vol. 1—Conference A: Computer Vision Image Processing., Proceedings of the 12th IAPR International Conference on. vol. 1. IEEE, 1994.

Hurteau, R., et al. "Laparoscopic surgery assisted by a robotic cameraman: concept and experimental results." Robotics and Automation, 1994. Proceedings., 1994 IEEE International Conference on. IEEE, 1994.

Raczkowsky, Jörg, et al. "System Concept for Collision-Free Robot Assisted Surgery Using Real-Time Sensing." Intelligent Autonomous Systems 12. Springer Berlin Heidelberg, 2013. 165-173.

"Endoscope Microscopy", Karl Storz Brochure, Aug. 2012.

"Karl Storz VITOM® HD", Karl Storz Brochure, Oct. 2010.

Mamelak, Adam N., et al. "A high-definition exoscope system for neurosurgery and other microsurgical disciplines: preliminary report." Surgical innovation 15.1 (2008): 38-46.

McLaughlin, Nancy, et al. "Endoneurosurgical resection of intraventricular and intraparenchymal lesions using the port technique." World neurosurgery 79.2 (2013): S18-e1.

Zudilova, Elena V. "A multi-modal interface for an interactive simulated vascular reconstruction system." Proceedings of the 4th IEEE International Conference on Multimodal Interfaces. IEEE Computer Society, 2002.

International Search Report ( PCT /CA2014/050271) dated Jul. 17, 2014.

Written Opinion (PCT/CA2014/050271) dated Jul. 17, 2014.

International Preliminary Report on Patentability (PCT/CA2014/050271) dated Jun. 8, 2015.

European Search Report from EP2967348 dated Jan. 11, 2017.

\* cited by examiner

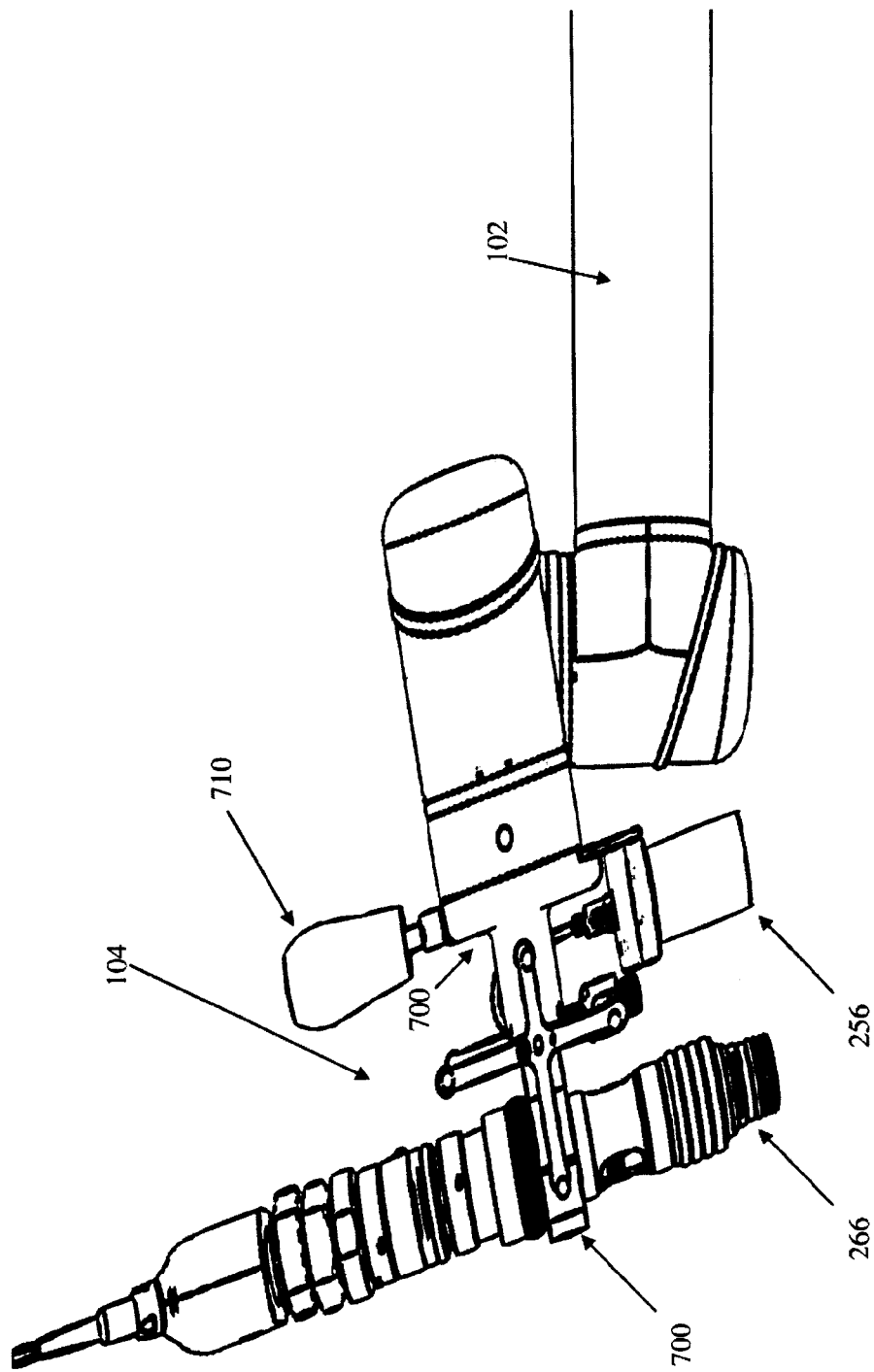

End Effector

End Effector

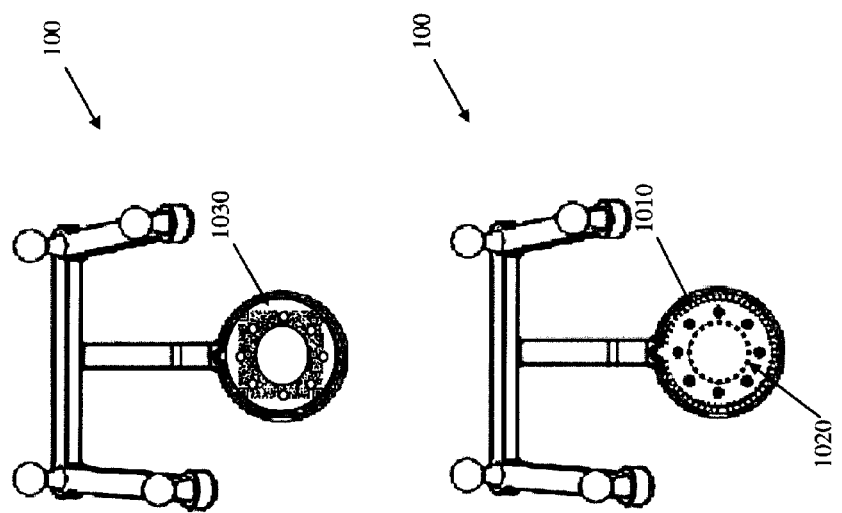

INTELLIGENT POSITIONING SYSTEM AND METHODS THEREFORE

This application is a National Phase application claiming the benefit of the International PCT Patent Application No. PCT/CA2014/050271, filed on Mar. 14, 2014, in English, which claims priority to U.S. Provisional Application No. 61/801,530, titled "SYSTEMS, DEVICES AND METHODS FOR PLANNING, IMAGING, AND GUIDANCE OF MINIMALLY INVASIVE SURGICAL PROCEDURES" and filed on Mar. 15, 2013, the entire contents of which are incorporated herein by reference.

This application claims priority to U.S. Provisional Application No. 61/801,530, titled "SYSTEMS, DEVICES AND METHODS FOR PLANNING, IMAGING, AND GUIDANCE OF MINIMALLY INVASIVE SURGICAL PROCEDURES" and filed on Mar. 15, 2013, the entire contents of which is incorporated herein by reference. This application also claims priority to U.S. Provisional Application No. 61/818,280, titled "SYSTEMS, DEVICES AND METHODS FOR PLANNING, IMAGING, AND GUIDANCE OF MINIMALLY INVASIVE SURGICAL PROCEDURES" and filed on May 1, 2013, the entire contents of which is incorporated herein by reference. This application also claims priority to U.S. Provisional Application No. 61/800,695, titled "INSERTABLE MAGNETIC RESONANCE IMAGING COIL PROBE FOR MINIMALLY INVASIVE CORRIDOR-BASED PROCEDURES" and filed on Mar. 15, 2013, the entire contents of which is incorporated herein by reference. This application also claims priority to U.S. Provisional Application No. 61/818,223, titled "IMAGING ASSEMBLY FOR ACCESS PORT-BASED MEDICAL PROCEDURES" and filed on May 1, 2013, the entire contents of which is incorporated herein by reference. This application also claims priority to U.S. Provisional Application No. 61/801,143, titled "INSERTABLE MAGNETIC RESONANCE IMAGING COIL PROBE FOR MINIMALLY INVASIVE CORRIDOR-BASED PROCEDURES" and filed on Mar. 15, 2013, the entire contents of which is incorporated herein by reference. This application also claims priority to U.S. Provisional Application No. 61/818,325, titled "INSERTABLE MAGNETIC RESONANCE IMAGING COIL PROBE FOR MINIMALLY INVASIVE CORRIDOR-BASED PROCEDURES" and filed on May 1, 2013, the entire contents of which is incorporated herein by reference. This application also claims priority to U.S. Provisional Application No. 61/801,746, titled "INSERT IMAGING DEVICE" and filed on Mar. 15, 2013, the entire contents of which is incorporated herein by reference. This application also claims priority to U.S. Provisional Application No. 61/818,255, titled "INSERT IMAGING DEVICE" and filed May 1, 2013, the entire contents of which is incorporated herein by reference. This application also claims priority to U.S. Provisional Application No. 61/800,155, titled "PLANNING, NAVIGATION AND SIMULATION SYSTEMS AND METHODS FOR MINIMALLY INVASIVE THERAPY" and filed Mar. 15, 2013, the entire contents of which is incorporated herein by reference. This application also claims priority to U.S. Provisional Application No. 61/924,993, titled "PLANNING, NAVIGATION AND SIMULATION SYSTEMS AND METHODS FOR MINIMALLY INVASIVE THERAPY" and filed Jan. 8, 2014, the entire contents of which is incorporated herein by reference.

FIELD

The present disclosure relates to mechanically assisted positioning of medical devices during medical procedures.

BACKGROUND

Intracranial surgical procedures present new treatment opportunities with the potential for significant improvements in patient outcomes. In the case of port-based surgical procedures, many existing optical imaging devices and modalities are incompatible due a number of reasons, including, for example, poor imaging sensor field of view, magnification, and resolution, poor alignment of the imaging device with the access port view, a lack of tracking of the access port, problems associated with glare, the presences of excessive fluids (e.g. blood or cranial spinal fluid) and/or occlusion of view by fluids. Furthermore, attempts to use currently available imaging sensors for port-based imaging would result in poor image stabilization. For example, a camera manually aligned to image the access port would be susceptible to misalignment by being regularly knocked, agitated, or otherwise inadvertently moved by personnel, as well as have an inherent settling time associated with vibrations. Optical port-based imaging is further complicated by the need to switch to different fields of view for different stages of the procedure. Additional complexities associated with access port-based optical imaging include the inability to infer dimensions and orientations directly from the video feed.

In the case of port-based procedures, several problems generally preclude or impair the ability to perform port-based navigation in an intraoperative setting. For example, the position of the access port axis relative to a typical tracking device employed by a typical navigation system is a free and uncontrolled parameter that prohibits the determination of access port orientation. Furthermore, the limited access available due to the required equipment for the procedure causes methods of indirect access port tracking to be impractical and unfeasible. Also, the requirement for manipulation of the access port intraoperatively to access many areas within the brain during a procedure makes tracking the spatial position and pose of the access port a difficult and challenging problem that has not yet been addressed prior to the present disclosure. Thus, there is a need to consider the use of an intelligent positioning system to assist in access port-based intracranial medical procedures and surgical navigation.

SUMMARY

A computer implemented method of adaptively and interoperatively configuring an automated arm used during a medical procedure, the method comprising:
  identifying a position and an orientation for a target in a predetermined coordinate frame;
  obtaining a position and an orientation for an end effector on the automated arm, the position and orientation being defined in the predetermined coordinate frame;
  obtaining a desired standoff distance and a desired orientation between the target and the end effector;
  determining a new desired position and a new desired orientation for the end effector from the position and orientation of the target and the desired standoff distance and the desired orientation; and
  moving the end effector to the new position and orientation.

The end effector may be an imaging device having a longitudinal axis. The target may be a surgical port having a longitudinal axis. The desired orientation may be such that the longitudinal axis of the imaging device may be colinear with the longitudinal axis of the surgical port.

The imaging device may be an external video scope.

The desired standoff distance may be between 10 cm and 80 cm.

Alternatively, the desired standoff distance may be obtained from a predetermined list. The predetermined list may be related to specific users. The standoff distance may be either increased or decreased responsive to a user command. The user command may be received from one of a foot pedal, a voice command and a gesture.

The method may include a user moving the end effector to a position and defining a distance between the end effector and the target as the desired standoff distance.

The target may be moved during the medical procedure and the method may include identifying an updated position and orientation of the target, determining an updated new position and orientation for the end effector and moving the end effector to the updated new position and orientation.

The updated position and orientation of the target may be obtained continuously and the updated new position and orientation may be determined continuously.

The end effector may be moved to the updated new position and orientation responsive to a signal from a user. The signal from the user may be received from a foot pedal. The signal from the user may be one of a voice command and a gesture.

The end effector may be moved to the new desired position and orientation responsive to predetermined parameters. The predetermined parameters may be that the target has not moved for more than a particular period of time. The particular period of time may be 15 to 25 seconds. The particular period of time may be defined by a user. The predetermined parameters may be that the orientation may be off co-axial by greater than a predetermined number of degrees. The predetermined number of degrees may be defined by a user. The target may be a port and the predetermined parameters may be less than predetermined percentage of the total field of view of the port. The predetermined percentage may be defined by a user.

An intelligent positioning system for adaptively and interoperatively positioning and end effector in relation to a target during a medical procedure including: a automated arm assembly including a multi-joint arm having a distal end connectable to the end effector; a detection system for detecting a position of the target; a control system and associated user interface operably connected to the automated arm assembly and operably connected to the detection system, the control system configured for: identifying a position and an orientation for a target in a predetermined coordinate frame; obtaining a position and an orientation for an end effector on the automated arm assembly, the position and orientation being defined in the predetermined coordinate frame; obtaining a desired standoff distance and a desired orientation between the target and the end effector; determining a new position and a new orientation for the end effector from the position and orientation of the target and the desired standoff distance and the desired orientation; and moving the end effector to the new position and orientation.

The system may include a visual display and images from the imaging device may be displayed on the visual display.

An automated arm assembly for use with an end effector, a target, a detection system and may be for use during a medical procedure, the automated arm assembly includes: a base frame; a multi-joint arm operably connected to the base frame and having a distal end that may be detachably connectable to the end effector; a weight operably connected to the base frame that provides a counterweight to the multi-joint arm; and a control system operably connected to the multi-joint arm and to the detection system which provide information relating to a position of the target and the control system determines a new position and orientation for the distal end of the multi-joint arm in relation to the position of the target; and whereby the distal end of the multi-joint arm may be moved responsive to information from the control system.

The automated arm assembly may include a tower attached to the base frame and extending upwardly therefrom, the multi-joint arm may be attached to the tower and extends outwardly therefrom. The arm may be movably upwardly and downwardly on the tower. The automated arm assembly may include a supporting beam with one end movably attached to the tower and the other end to the automated arm. The multi-joint arm may have at least six degrees of freedom. The automated arm assembly may be moved manually. The base frame may include wheels.

The end effector may be tracked using the detection system. The multi-joint arm may include tracking markers which are tracked using the detection system. The automated arm assembly may include a radial arrangement attached to the distal end of the multi-joint arm and the end effector may be movable attached to the radial arrangement whereby the end effector moves along the radial arrangement responsive to information from the control system.

The automated arm assembly may include a joy stick operably connected to the control system and movement of the multi-joint arm may be controllable by the joy stick.

The end effector may be one of an external video scope, an abrasion laser, a gripper, an insertable probe or a micromanipulator. The end effector may be a first end effector and further including a second end effector attachable proximate to the distal end of the multi-joint arm. The second end effector may be wide angle camera.

The control system may constrain the movement of the multi-joint arm based on defined parameters. The defined parameters may include space above patient, floor space, maintaining surgeon line of sight, maintaining tracking camera line of sight, mechanical arm singularity, self-collision avoidance, patient collision avoidance, base orientation, and a combination thereof.

The automated arm assembly may include a protective dome attached to the multi-joint arm and the distal end of the multi-joint arm may be constrained to move only within the protective dome. A virtual safety zone may be defined by the control system and the distal end of the multi-joint arm may be constrained to move only within the safety zone.

An alignment tool for use with a surgical port including: a tip for insertion into the surgical port; and a generally conical portion at the distal end of the tip and attached such that the conical portion may be spaced outwardly from the end of port when the tip may be fully inserted into the portion. The conical portion may be made of a plurality of circular annotation.

In some embodiments, intelligent positioning systems (and associated methods) for supporting access port-based procedures are disclosed that include the following components: one or more imaging devices; a tracked and guided external automated arm configured to support one or more of the imaging devices; one or more tracking devices or mechanisms; one or more tracked markers or tracked marker assembly's; a navigation system configured to accept preoperative and/or intraoperative data; and an intelligent positioning system to control the pose and position of the automated arm.

In some embodiments, a software system is provided that includes a user interface for performing surgical procedures, where the user interface includes visualization and processing of images based on tracked devices, and intracranial images (optionally preoperative and intraoperative). The combined result is an efficient imaging and surgical interventional system that maintains the surgeon in a preferred state (e.g. one line of sight, bi-manual manipulation) that is suitable or tailored for performing surgery more effectively.

In some embodiments, as described below, the access port may be employed to provide for an optical visualization path for an imaging device. The imaging device acquires a high resolution image of the surgical area of interest and provides a means for the surgeon to visualize this surgical area of interest using a monitor that displays said image. The image may be still images or video stream.

In some embodiments, a system is provided that includes an intelligent positioning system, that is interfaced with the navigation system for positioning and aligning one or more imaging devices relative to (and/or within) an access port. In order to achieve automated alignment, tracking devices may be employed to provide spatial positioning and pose information in common coordinate frame on the access port, the imaging device, the automated arm, and optionally other surgically relevant elements such as surgical instruments within the surgical suite. The intelligent positioning system may provide a mechanically robust mounting position configuration for a port-based imaging sensor, and may enable the integration of pre-operative images in a manner that is useful to the surgeon. A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 4A-E are exemplary embodiment of various components in an intelligent positioning system 4B

FIG. 10A-B is an illustration depicting tool characteristics that can be utilized in optical detection methods.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

As used herein the term "Navigation system", refers to a surgical operating platform which includes within it an Intelligent Positioning System as described within this document.

As used herein the term "Imaging sensor", refers to an imaging system which may or may not include within it an Illumination source for acquiring the images.

As used herein, the term "tracking system", refers to a registration apparatus including an operating platform which may be included as part of or independent of the intelligent positioning system which.

Several embodiments of the present disclosure seek to address the aforementioned inadequacies of existing devices and methods to support access port-based surgical procedures.

Figure 16A:
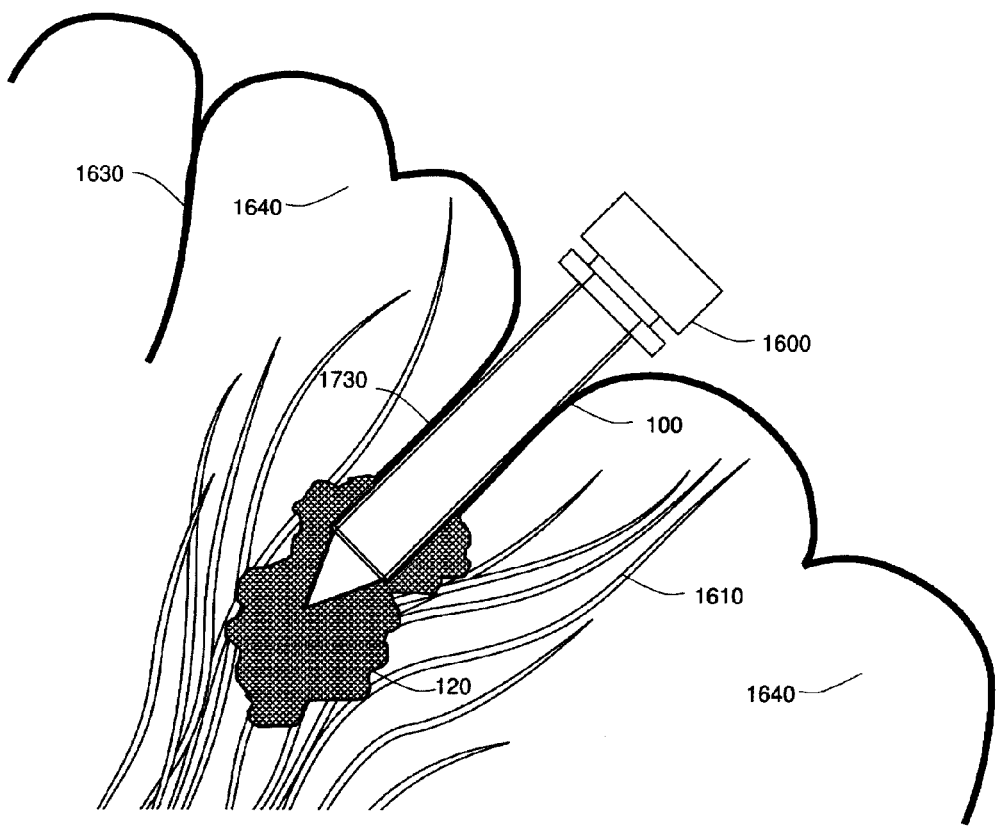
FIG. 16A-D are exemplary embodiments illustrating a port with introducer during cannulation into the brain.
Figure 16B:
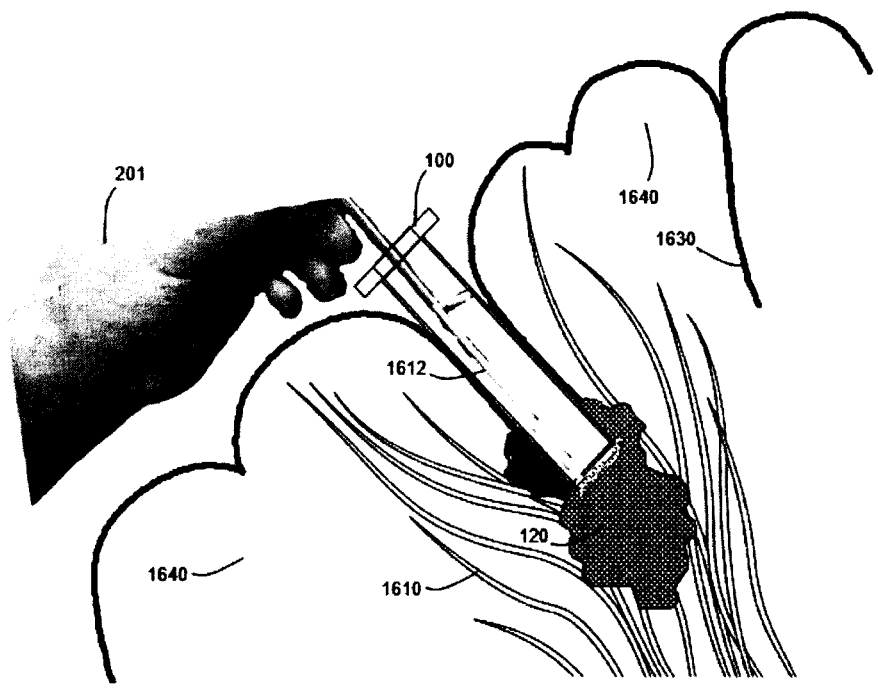

Minimally invasive brain surgery using access ports is a recently conceived method of performing surgery on brain tumors previously considered inoperable. One object of the present invention is to provide a system and method to assist in minimally invasive port-based brain surgery. To address intracranial surgical concerns, specific products such as the NICO BrainPath™ port have been developed for port-based surgery. As seen in FIG. 16A, port 100 comprises of a cylindrical assembly formed of an outer sheath. Port 100 may accommodate introducer 1600 which is an internal cylinder that slidably engages the internal surface of port 100. Introducer 1600 may have a distal end in the form of a conical atraumatic tip to allow for insertion into the sulci folds 1630 of the brain. Port 100 has a sufficient diameter to enable manual manipulation of traditional surgical instruments such as suctioning devices, scissors, scalpels, and cutting devices as examples. FIG. 16B shows an exemplary embodiment where surgical instrument 1612 is inserted down port 100.

Figure 1:
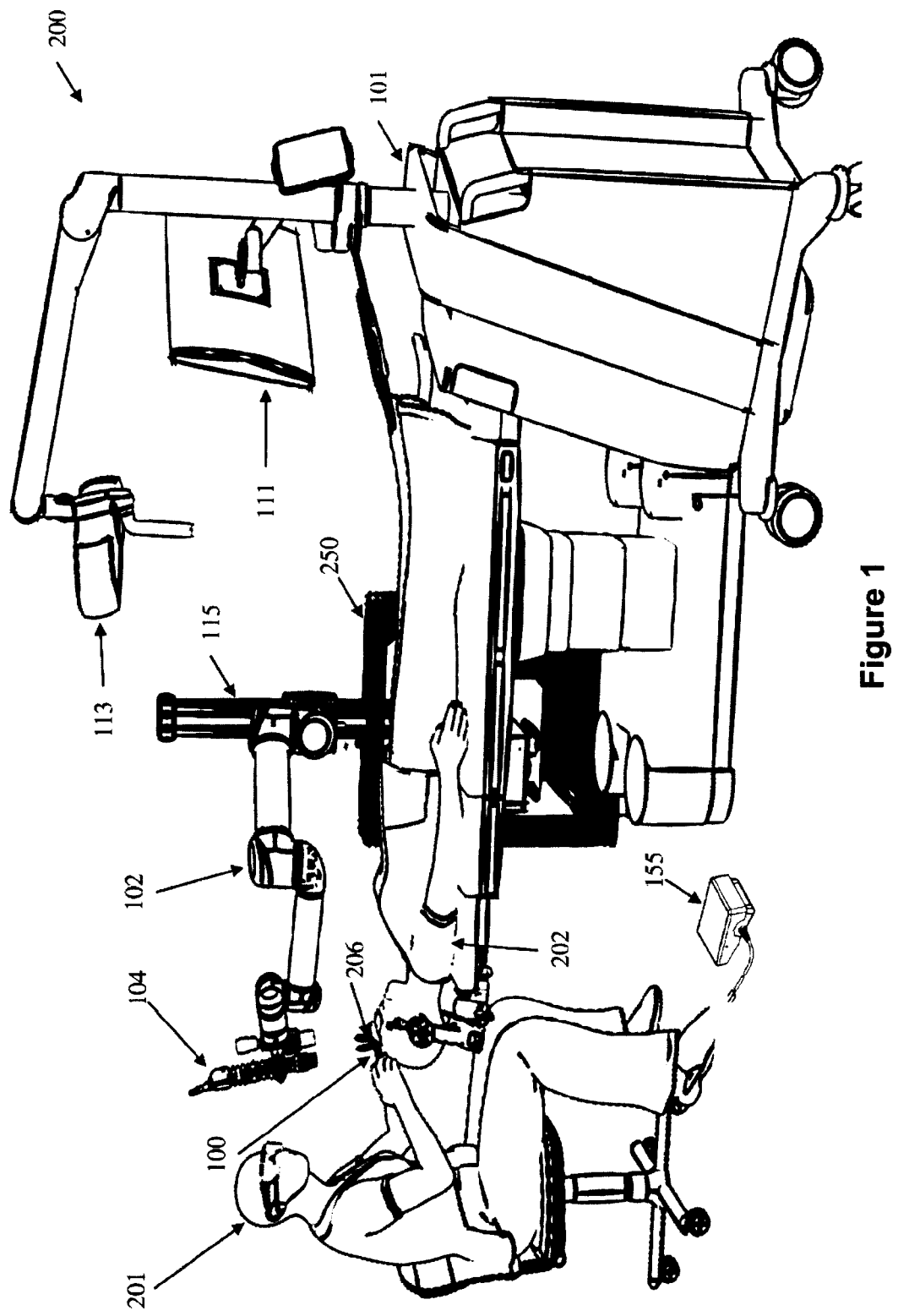
FIG. 1 is an exemplary embodiment illustrating system components of an exemplary surgical system used in port based surgery

FIG. 1 is a diagram illustrating components of an exemplary surgical system used in port based surgery. FIG. 1 illustrates a navigation system 200 having an equipment tower 101, tracking system 113, display 111, an intelligent positioning system 250 and tracking markers 206 used to tracked instruments or an access port 100. Tracking system 113 may also be considered an optical tracking device or tracking camera.

In FIG. 1, a surgeon 201 is performing a tumor resection through a port 100, using an imaging device 104 to view down the port at a suffcient magnification to enable enhanced visibility of the instruments and tissue. The imaging device 104 may be an external scope, videoscope, wide field camera, or an alternate image capturing device. The imaging sensor view is depicted on the visual display 111 which surgeon 201 uses for navigating the port's distal end through the anatomical region of interest.

Figure 5A:
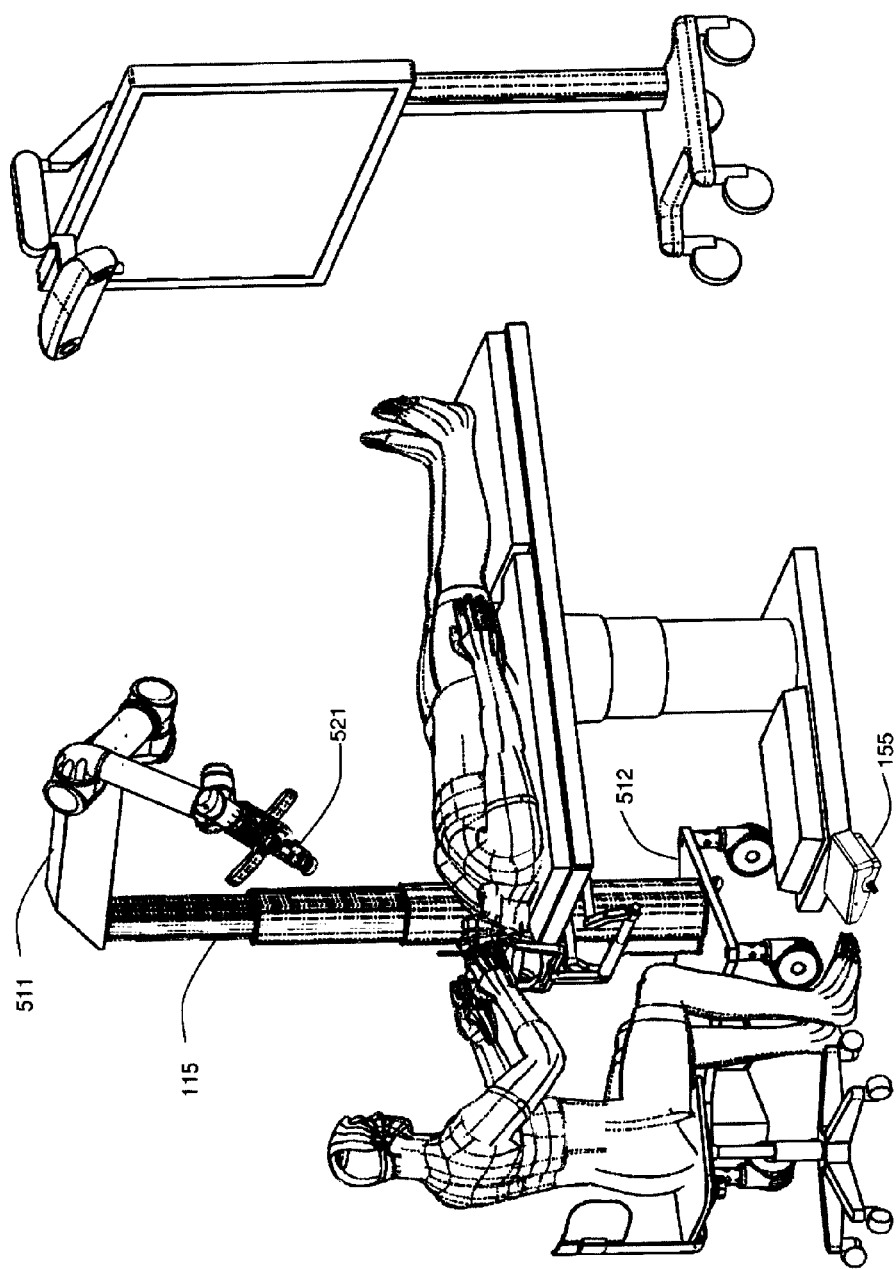
FIG. 5A-B are exemplary embodiments of an intelligent positioning system including a lifting column.

An intelligent positioning system 250 comprising an automated arm 102, a lifting column 115 and an end effector 104, is placed in proximity to patient 202. Lifting column 115 is connected to a frame of intelligent positioning system 250. As seen in FIG. 1, the proximal end of automated mechanical arm 102 (further known as automated arm herein) is connected to lifting column 115. In other embodiments, automated arm 102 may be connected to a horizontal beam 511 as seen in FIG. 5A, which is then either connected to lifting column 115 or the frame of the intelligent positioning system 250 directly. Automated arm 102 may have multiple joints to enable 5, 6 or 7 degrees of freedom.

End effector 104 is attached to the distal end of automated arm 102. End effector 104 may accommodate a plurality of instruments or tools that may assist surgeon 201 in his procedure. End effector 104 is shown as an external scope, however it should be noted that this is merely an example embodiment and alternate devices may be used as the end effector 104 such as a wide field camera 256 (shown in FIG. 2), microscope and OCT (Optical Coherence Tomography) or other imaging instruments. In an alternate embodiment multiple end effectors may be attached to the distal end of automated arm 102, and thus assist the surgeon in switching between multiple modalities. For example, the surgeon may want the ability to move between microscope, and OCT with stand-off optics. In a further example, the ability to attach a second more accurate, but smaller range end effector such as a laser based ablation system with micro-control may be contemplated.

Figure 2:
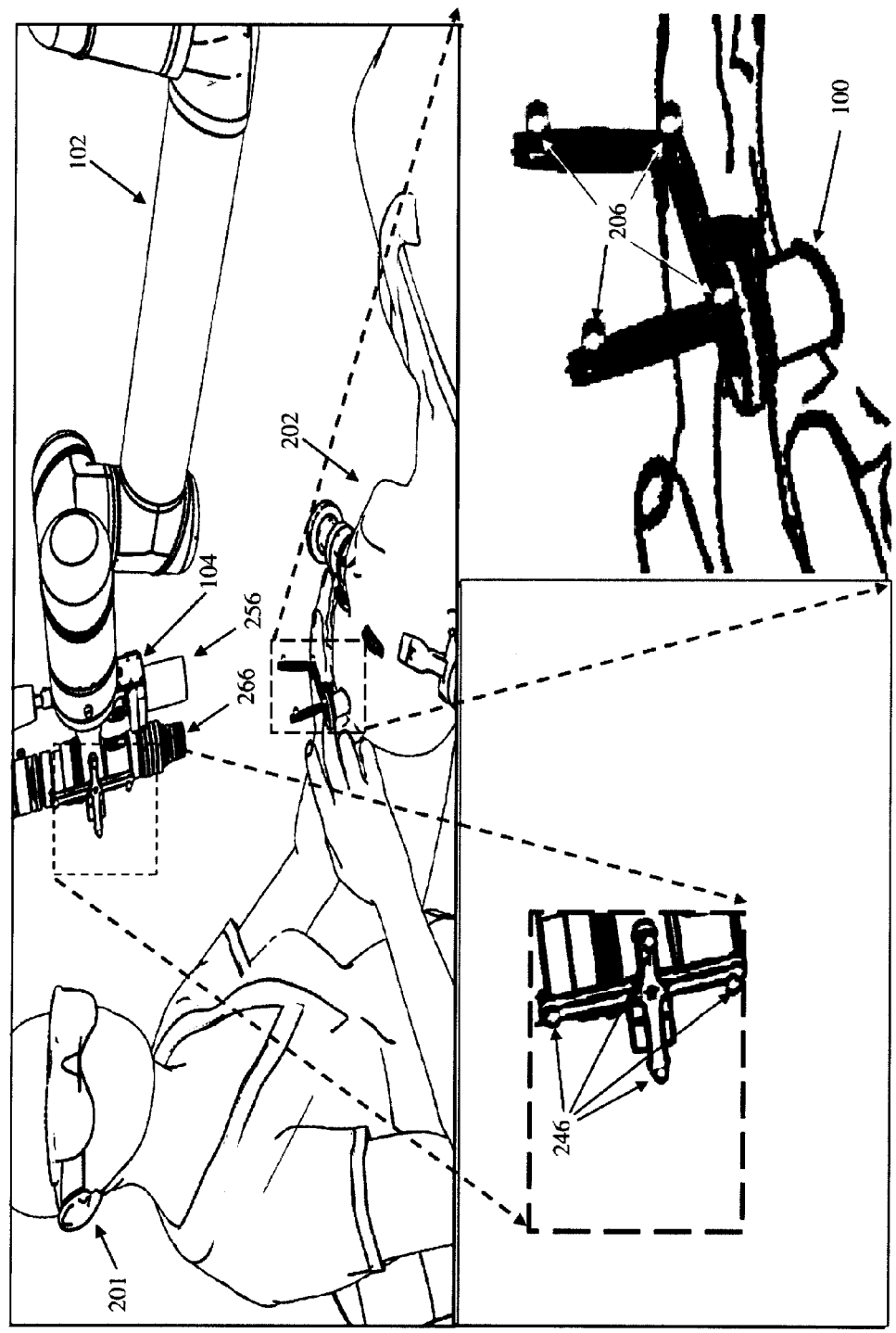
FIG. 2 is an exemplary embodiment illustrating various detailed aspects of a port based surgery as seen in FIG. 1.

The intelligent positioning system 250 receives as input the spatial position and pose data of the automated arm 102 and target (for example the port 100) as determined by tracking system 113 by detection of the tracking markers 246 on the wide field camera 256 on port 100 as shown in FIG. 2. Further, it should be noted that the tracking markers 246 may be used to track both the automated arm 102 as well as the end effector 104 either collectively (together) or independently. It should be noted that the wide field camera 256 is shown in this image and that it is connected to the external scope 266 and the two imaging devices together form the end effector 104. It should additionally be noted that although these are depicted together for illustration of the diagram that either could be utilized independent of the other, for example as shown in FIG. 5A where an external video scope 521 is depicted independent of the wide field camera.

Figure 6A:
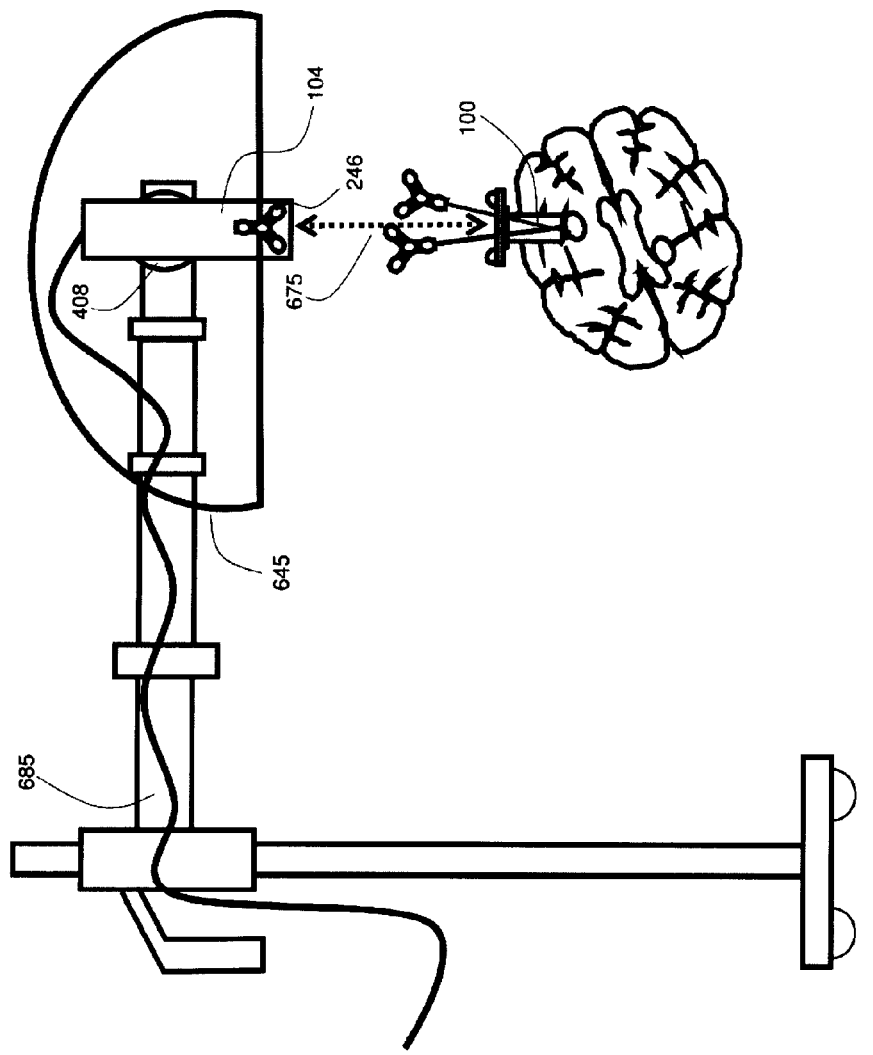
FIG. 6A-C are exemplary embodiments illustrating alignment of an imaging sensor with a target (port).
Figure 6B:
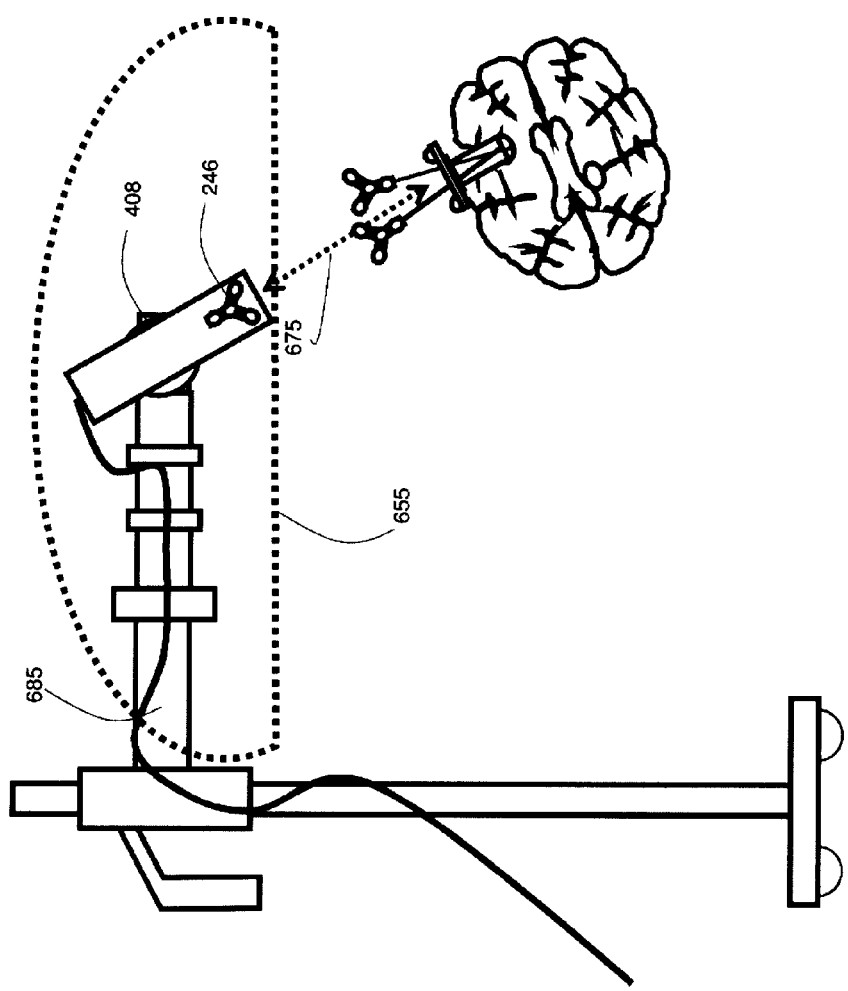

Intelligent positioninng system 250 computes the desired joint positions for automated arm 102 so as to maneuver the end effector 104 mounted on the automated arm's distal end to a predetermined spatial position and pose relative to the port 100. This redetermined relative spatial position and pose is termed the "Zero Position" and is described in further detail below and is shown in FIG. 6A-B where the imaging sensor and port are axially allligned 675 having a linear line of sight.

Further, the intelligent positioning system 250, optical tracking device 113, automated arm 102, and tracking markers 246 and 206 form a feedback loop. This feedback loop works to keep the distal end of the port (located inside the brain) in constant view and focus of the end effector 104 given that it is an imaging device as the port position may be dynamically manipulated by the surgeon during the procedure. Intelligent positioning system 250 may also include foot pedal 155 for use by the surgeon 201 to align of the end effector 104 (i.e., a videoscope) of automated arm 102 with the port 100. Foot pedal 155 is also found in FIGS. 5A, 5C and 7.

Figure 3:
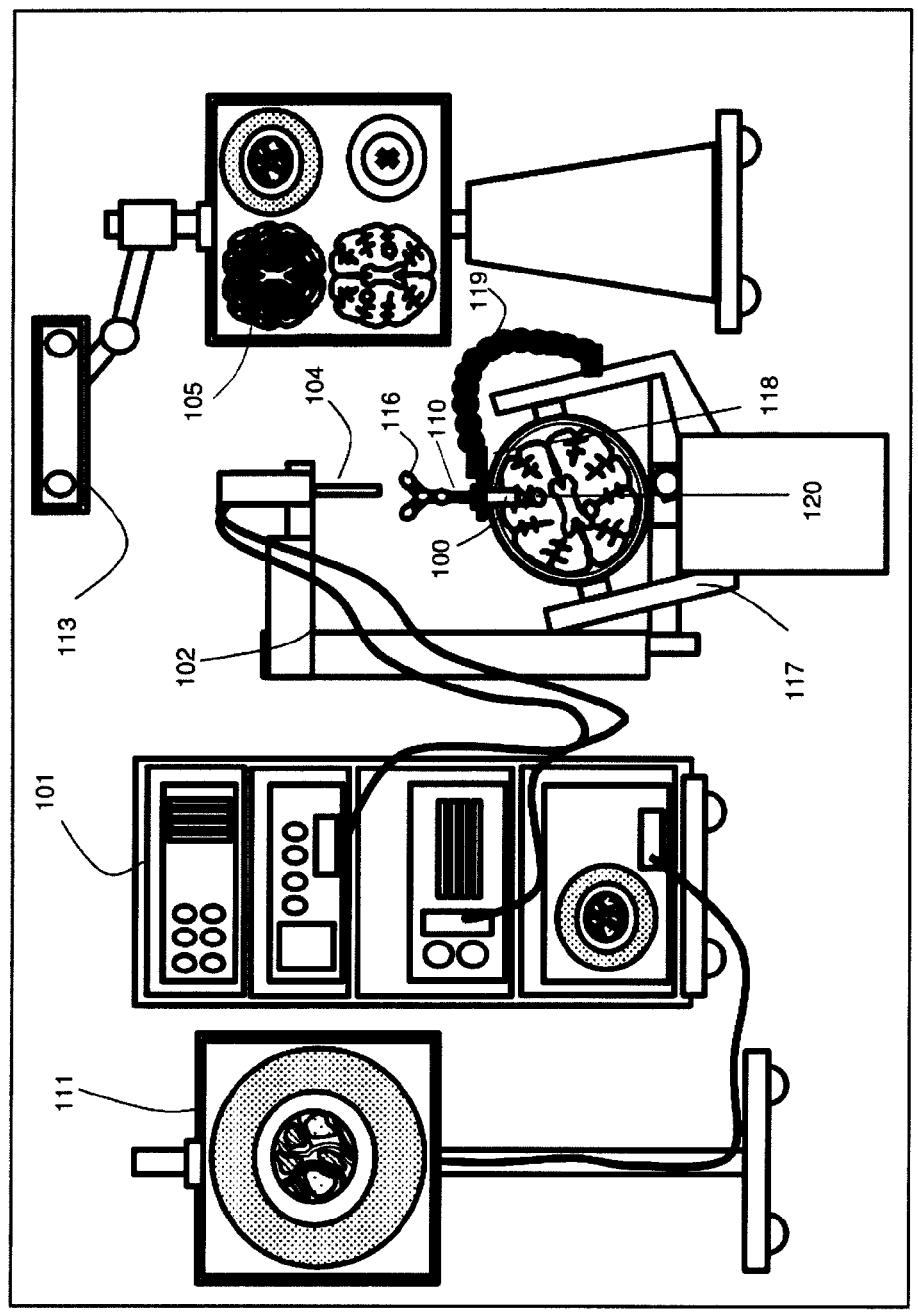
FIG. 3 is an exemplary embodiment illustrating system components of an exemplary navigation system.

FIG. 3 is a diagram illustrating system components of an exemplary navigation system for port-based surgery. In FIG. 3, the main components to support minimally invasive access port-based surgery are presented as separated units. FIG. 1 shows an example system including a monitor 111 for displaying a video image, an optical equipment tower 101, which provides an illumination source, camera electronics and video storage equipment, an automated arm 102, which supports an imaging sensor 104. A patient's brain is held in place by a head holder 117, and inserted into the head is an access port 100 and introducer 1600 as shown in FIG. 16A. The introducer 1600 may be replaced by a tracking probe (with attached tracking marker 116) or a relevant medical instrument such as 1612 used for port-based surgery. The introducer 1600 is tracked using a tracking system 113, which provides position and orientation information for tracked devices to the intelligent positioning system 250.

Figure 16C:
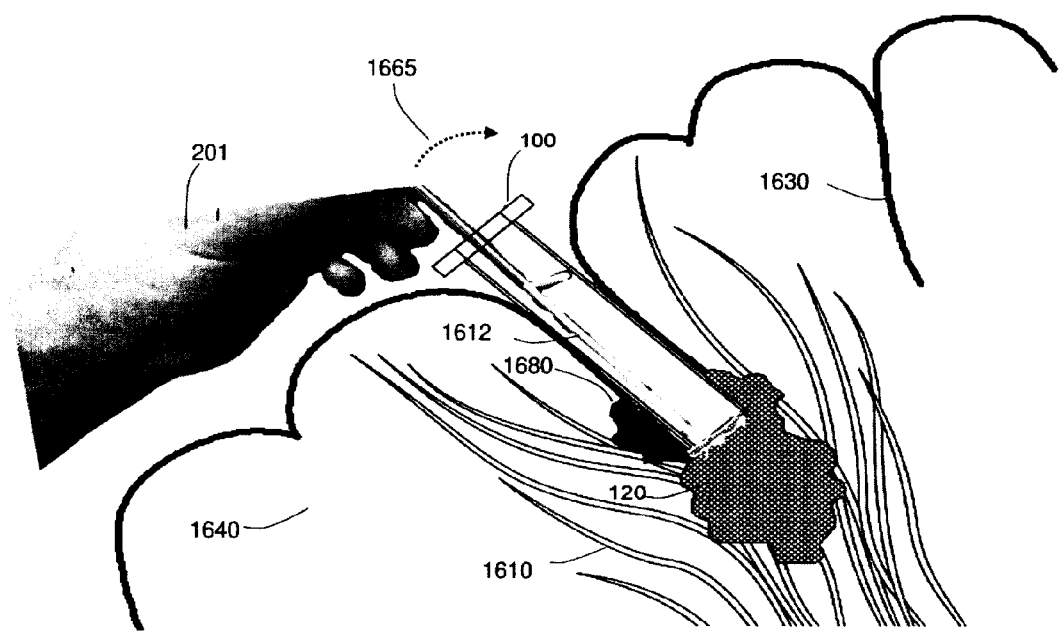
Figure 16D:
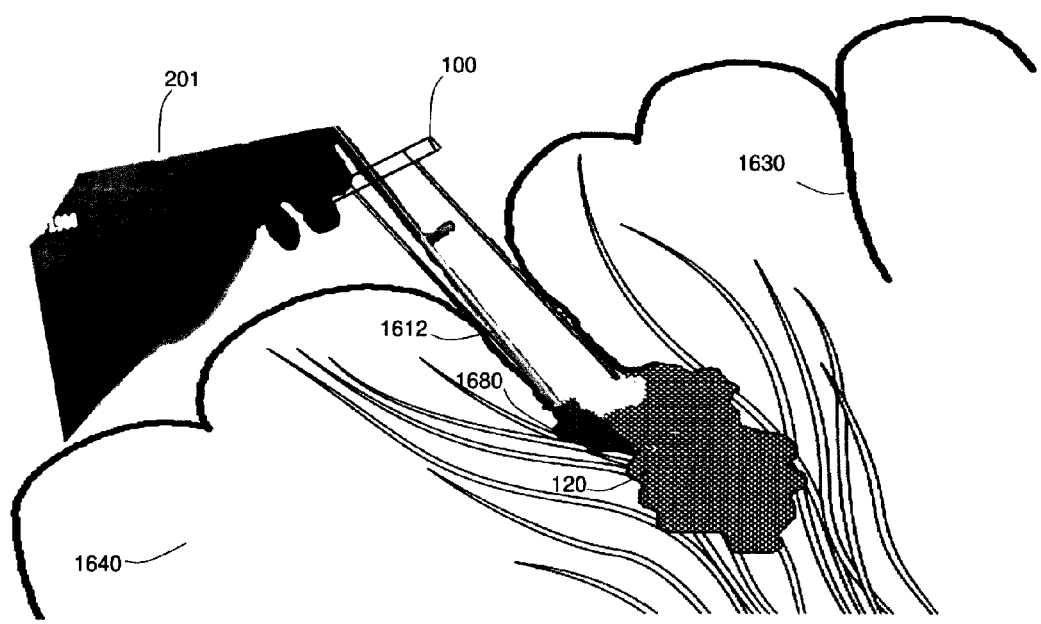

An example of the surgeon dynamically manipulating the port 100 is shown in FIG. 16D. In FIG. 16C-D, a port based tumor resection is being performed within the brain 1640. The surgeon 201 will typically maneuver the port 100 to actively search for and provide access to as much of the tumor 120 or equivalently unhealthy tissue as possible in order to resect it using a medical instrument 1612. In FIG. 16C there is a section of the tumor 1680 that is not accessible given the positioning of the port 100. In order to access that section of the tumor 1680, the surgeon 201 maneuvers the port 100 through a rotation as shown by the dashed arrow 1665. Now referring to FIG. 16D this maneuvering of the port 100 allows the surgeon 201 to access the previously unaccessible section 1680 of the tumor 120 in order to resect it using the medical instrument 1612.

Arm Description

The method according to the invention described herein is suitable both for an individual automated arm of a multi-arm automated system and for the aforementioned single automated arm system. The gain in valuable operating time, shorter anesthesia time and simpler operation of the device are the direct consequences of the system according to an examplery version of the invention as shown in FIG. 1.

Figure 4B:
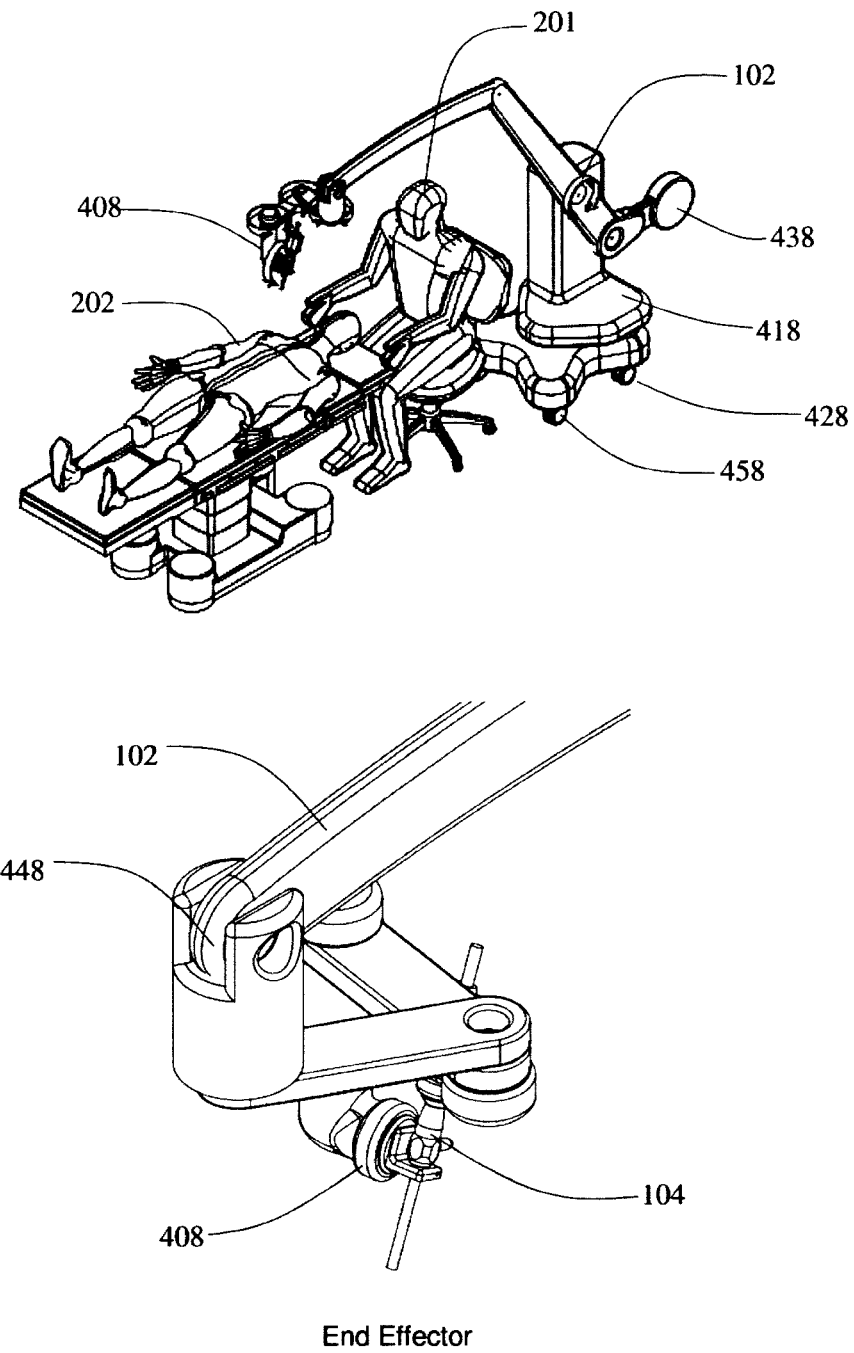
Figure 4C:
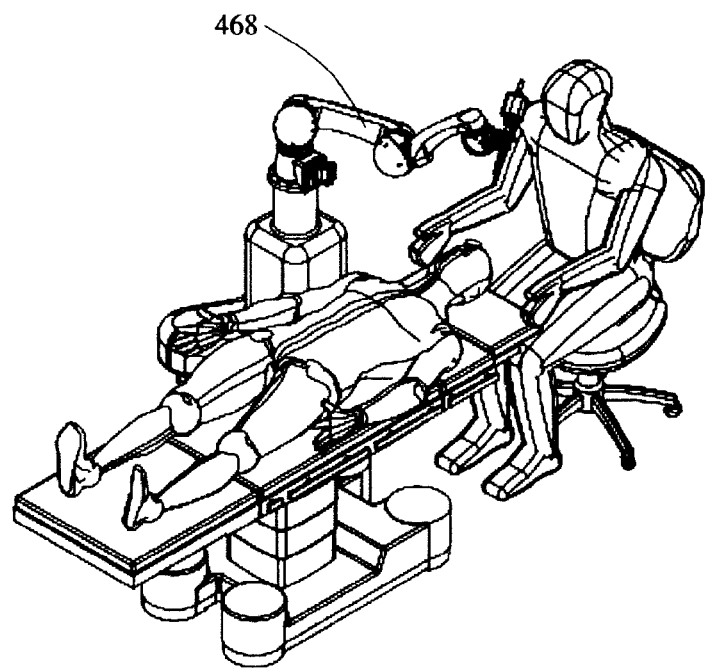
Figure 4C:
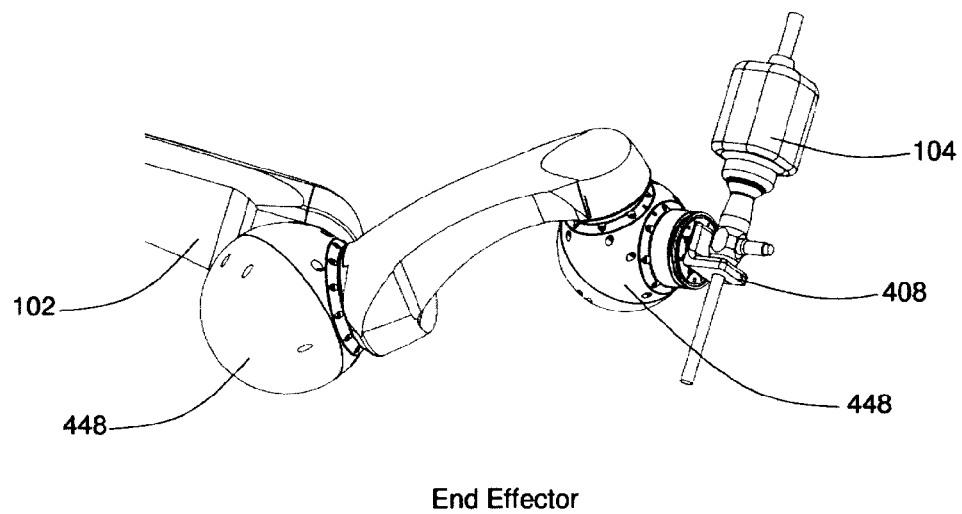

FIGS. 4B and 4C illustrate alternate example embodiments of automated arms. In FIG. 4B the distal end 408 is positioned using an extended automated arm 102 that extends over the surgeon 201. The base 428 of this arm 102 may be positioned away from the patient 202 to provide clear access to the patient 202 lying on the surgical bed. The base 428 may be equipped with caster wheel 458 to facilitate mobility within the operating room. A counter weight 438 may be provided to mechanically balance the system and minimize the load on the actuators (this weight serving the same function as weight 532 in FIG. 5B). The distal end 408 can be arbitrarily positioned due to the presence of a redundant number of degrees of freedom. Joints, such as rotating base 418 in FIG. 4B and joint 448 provide these degrees of freedom. The imaging device 104 may be attached to the final joint or equivalently the distal end 408.

FIG. 4C illustrates another embodiment where a commercially available arm 102 may be used. Again, joints 448 provide redundant number of degrees of freedom to aid in easy movement of the distal end 408. In another embodiment, the distal end may have connectors that can rigidly hold an imaging device while facilitating easy removal of the device to interchange with other imaging devices.

Figure 4D:
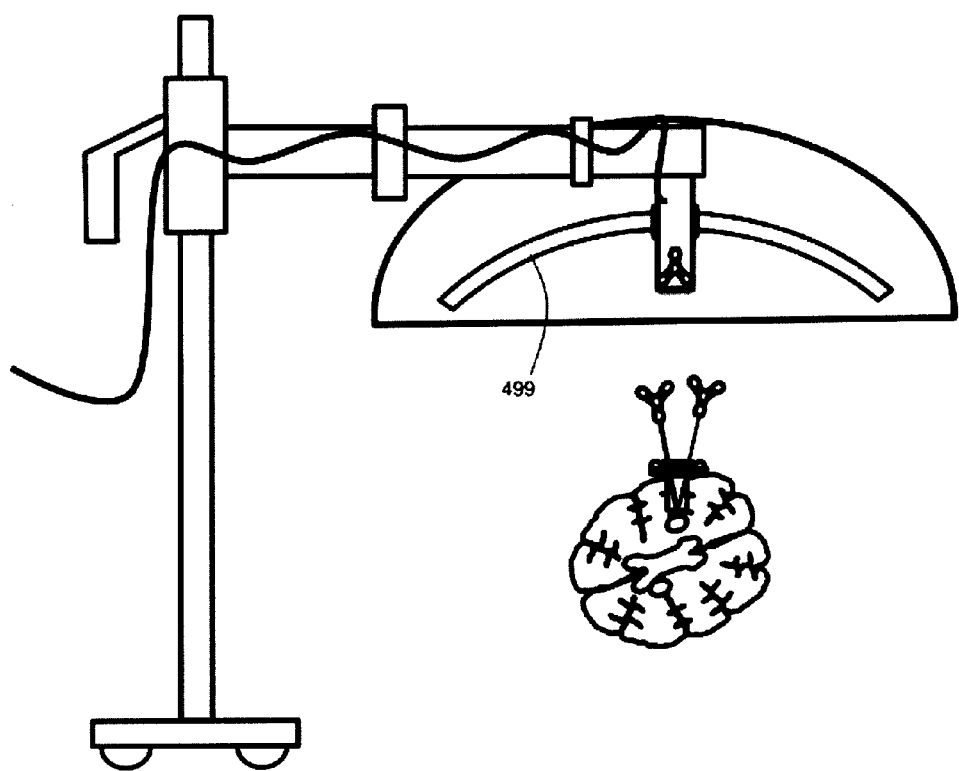

FIG. 4D illustrates an alternative embodiment in which a radial arrangement 499 is employed for the distal end. This arrangement allows the end effector to slide along the curved segment 499 to provide a unique degree of freedom.

It should be noted that while FIGS. 4B-C illustrate a floor-standing design, this embodiment is not intended to limit the scope of the disclosure, and it is to be appreciated that other configurations may be employed. For example, alternative example configurations include a structure that is supported from the ceiling of the operating room; a structure extending from a tower intended to encase imaging instrumentation; and by rigidly attaching the base of the automated arm to the surgical table.

In some embodiments, multiple arms may be used simultaneously for one procedure and navigated from a single system. In such an embodiment, each distal end may be separately tracked so that the orientation and location of the devices is known to the intelligent positioning system and the position and/or orientation of the mounted distal end devices may be controlled by actuating the individual automated arms based on feedback from the tracking system. This tracking can be performed using any of the methods and devices previously disclosed.

In an alternate embodiment, the head of the patient may be held in a compliant manner by a second automated arm instead of a rigid frame 117 illustrated in FIG. 1. The automated head support arm can be equipped with force sensing actuators that provide signals that enable the tracking of minor movement of the head. These sensed position of the head may be provided as feedback to control the relative position of the first automated arm, and correspondingly position the distal end used to mount the device (such as an imaging sensor). This coupling of the head holding assembly and the imaging system may aid in reducing movement artefacts while providing patient comfort. Patient comfort will be greatly enhanced due to the elimination of sharp points used in the traditional head immobilization systems.

In current surgical procedures, available operating room space around the patient being operated on is a scarce commodity due to the many personnel and devices needed to perform the surgery. Therefore the space required by the device around the surgical bed being minimized is optimal.

In an embodiment the space required by the automated arm may be minimized comparatively to presently used surgical arms through the use of a cantilevered design. This design element allows the arm to be suspended over the patient freeing up space around the patient where most automated arms presently occupy during the surgical procedures. FIG. 5(a) shows such a cantilevered arm 511, where the arm anchor is a weighted base 512. This allows the arm to be suspended with minimized risk of tipping, as the weighted base offsets the arm.

Figure 4E:
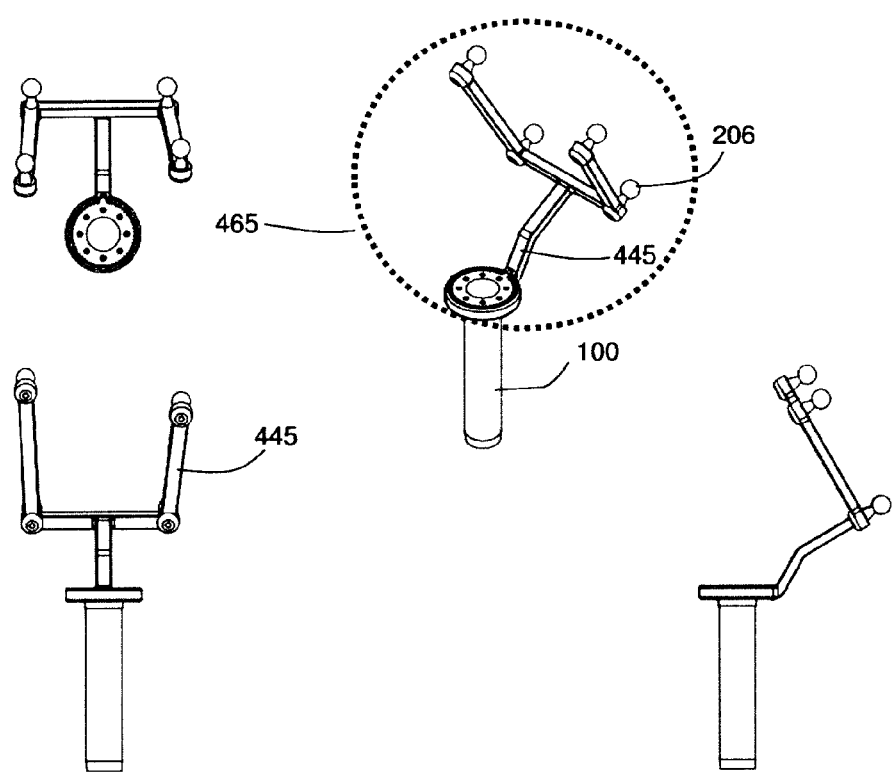
Figure 5B:
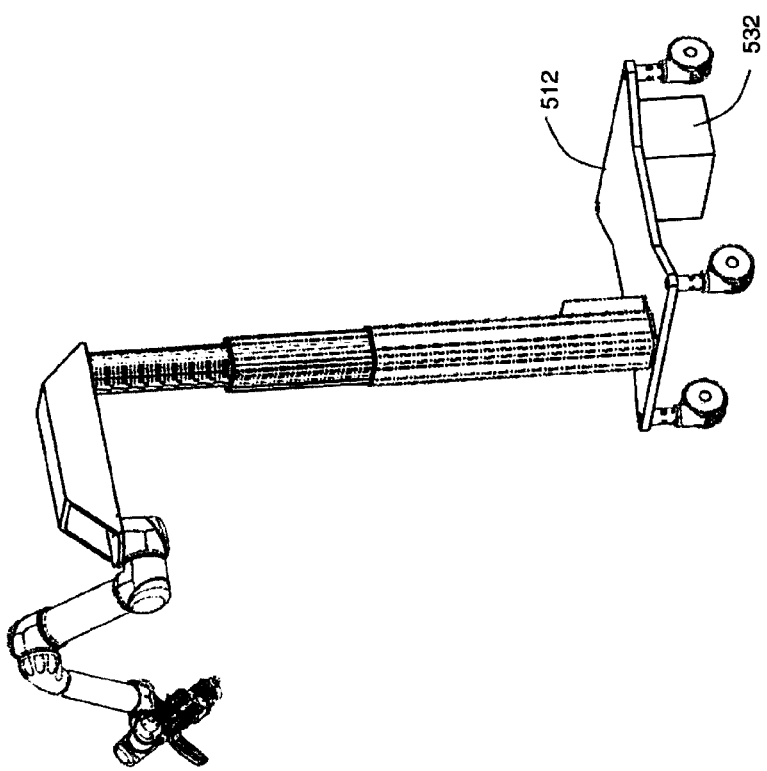

In another embodiment the space required by the automated arm may be minimized comparatively to presently used surgical arms through the use of a concentrated counterweight 532 attached to the base of the automated arm 512, which takes up a small footprint not only in its height dimension but as well as the floor area in which it occupies. It should be noted that the reduction in area used in the height direction is space that can be occupied by other devices or instruments in the OR such as a surgical tool table. In addition the smaller area required by the base of this automated arm can allow for less restricted movement of personnel around the patient as well as more supplementary device and instruments to be used. FIG. 5B shows such a base which utilizes minimum space and has a concentrated weight 532. The automated arm in this example is held at a particular height by a lifting column 115, as this design requires minimal space. In addition some alternate embodiments that could be used for the lifting column 115 include a 4-bar arm, a scissor lift and pneumatic pistons Tracking In an embodiment as illustrated in FIG. 2 and FIG. 4E, tracking markers 206 may be fitted to port 100. The spatial position and pose of the port (target) are determined using the tracking markers 206 and are then detected by the tracking device 113 shown in FIG. 1 and registrered within a common coordinate frame. From the spatial position and pose of the port 100 (target), the desired position of the end effector 104 and the automated arm 102 may be determined. As shown as FIG. 7, lifting column 115 may raise or lower automated arm 102 from an actual position 700 to a desired position 710. For this purpose, it is possible, for example, for the tracking markers 246 located on an assembly as shown in FIG. 2 to be fitted on the automated arm 102, so that its spatial position and pose in the operating room (OR) can thus be determined by the tracking device 113 and the intelligent positioning system 250. Further, the automated arms spatial position and pose can also be determined using position encoders located in the arm that enable encoding of joint angles. These angles combined with the lengths of the respective arm segments can be used to infer the spatial position and pose of the end effector 104 or equivalently the imaging sensor (for example the exoscope 521 shown in FIG. 5A) relative to base 512 of intelligent positioning system 250. Given the automated arms base's 512 spatial position and pose is registered to the common coordinate frame.

In an embodiment, passive tracking markers such as the reflective spherical markers 206 shown in FIG. 2 are seen by the tracking device 113 to give identifiable points for spatially locating and determining the pose of a tracked object (for example a port 100 or external scope 521) to which the tracking markers are connected to.

As seen in FIG. 4E, a medical instrument (target) such as port 100 may be tracked by a unique, attached marker assembly 465 which is used to identify the corresponding medical instrument inclusive of its spatial position and pose as well as its 3D volume representation to a navigation system 200, within the common coordinate frame. In FIG. 4E Port 100 is rigidly connected to tracking marker assembly 465 which is used to determine its spatial position and pose in 3D. Typically, a minimum of 3 spheres are placed on a tracked medical instrument or object to define it. In the exemplary embodiment of FIG. 4E, 4 spheres are used to track the target object (port).

The navigation system typically utilizes a tracking system. Locating tracking markers is based, for example, on at least three tracking markers 206 that are arranged statically on the target (for example port 100) as shown in FIG. 2 on the outside of the patient's body 202 or connected thereto. A tracking device 113 as shown in FIG. 1 detects the tracking markers 206 and determines their spatial position and pose in the operating room which is then registered to the common coordinate frame and subsequently stored by the navigation system.

An advantageous feature of an optical tracking device is the selection of markers that can be segmented very easily and therefore detected by the tracking device. For example, infrared (IR)-reflecting markers and an IR light source can be used. Such an apparatus is known, for example, from tracking devices such as the "Polaris" system available from Northern Digital Inc. In a further embodiment, the spatial position of the port (target) 100 and the position of the automated arm 102 are determined by optical detection using the tracking device. Once the optical detection occurs the spatial markers are rendered optically visible by the device and their spatial position and pose is transmitted to the intelligent positioning system and to other components of the navigation system.

In a preferred embodiment, the navigation system or equivalently the intelligent positioning system may utilize reflectosphere markers 206 as shown in FIG. 4E in combination with a tracking device, to determine spatial positioning of the medical instruments within the operating theater. Differentiation of the types of tools and targets and their corresponding virtual geometrically accurate volumes could be determined by the unique individual specific orientation of the reflectospheres relative to one another on a marker assembly 445. This would give each virtual object an individual identity within the navigation system. These individual identifiers would relay information to the navigation system as to the size and virtual shape of the instruments within the system relative to the location of their respective marker assemblies. The identifier could also provide information such as the tools central point, the tools central axis, etc. The virtual medical instrument may also be determinable from a database of medical instruments provided to the navigation system.

Other types of tracking markers that could be used would be RF, EM, LED (pulsed and un-pulsed), glass spheres, reflective stickers, unique structures and patterns, where the RF and EM would have specific signatures for the specific tools they would be attached to. The reflective stickers, structures and patterns, glass spheres, and LEDs could all be detected using optical detectors, while RF and EM could be picked up using antennas. Advantages to using EM and RF tags would include removal of the line of sight condition during the operation, where using optical system removes the additional noise from electrical emission and detection systems.

In a further embodiment, printed or 3-D design markers could be used for detection by the imaging sensor provided it has a field of view inclusive of the tracked medical instruments. The printed markers could also be used as a calibration pattern to provide (3-D) distance information to the imaging sensor. These identification markers may include designs such as concentric circles with different ring spacing, and/or different types of bar codes. Furthermore, in addition to using markers, the contours of known objects (i.e., side of the port) could be made recognizable by the optical imaging devices through the tracking system as described in the paper [Lepetit, Vincent, and Pascal Fua. *Monocular model-based* 3D *tracking of rigid objects*. Now Publishers Inc, 2005]. In an additional embodiment, reflective spheres, or other suitable active or passive tracking markers, may be oriented in multiple planes to expand the range of orientations that would be visible to the camera.

In an embodiment illustrating a port used in neurosurgery, as described above is shown by way of example in FIG. 16B, which shows an access port 100 that has been inserted into the brain, using an introducer 1600, as previously described. In the illustration shown in FIG. 16B, the introducer has been removed. The same access port 100 shown in FIG. 4E includes a plurality of tracking elements 206 as part of a tracking marker assembly 465. The tracking marker assembly is comprised of a rigid structure 445 to supports the attachment of a plurality of tracking elements 206. The tracking markers 206 may be of any suitable form to enable tracking as listed above. In some embodiments, assembly 465 may be attached to access port 100, or integrated as part of access port 100. It is to be understood that the orientation of the tracking markers may be selected to provide suitable tracking over a wide range of relative medical instrument positional orientations and poses, and relative imaging sensor positional orientations and poses.

Safety System

A challenge with automated movement in a potentially crowded space, such as the operating room, may be the accidental collision of any part of the automated arm with surgical team members or the patient. In some embodiments, this may be avoided by partially enclosing the distal end 408 within a transparent or translucent protective dome 645 as shown in FIG. 6A that is intended to prevent accidental contact of the end effector 104 or equivalently the imaging sensor 521 with surgical team members or the patient.

Figure 6C:
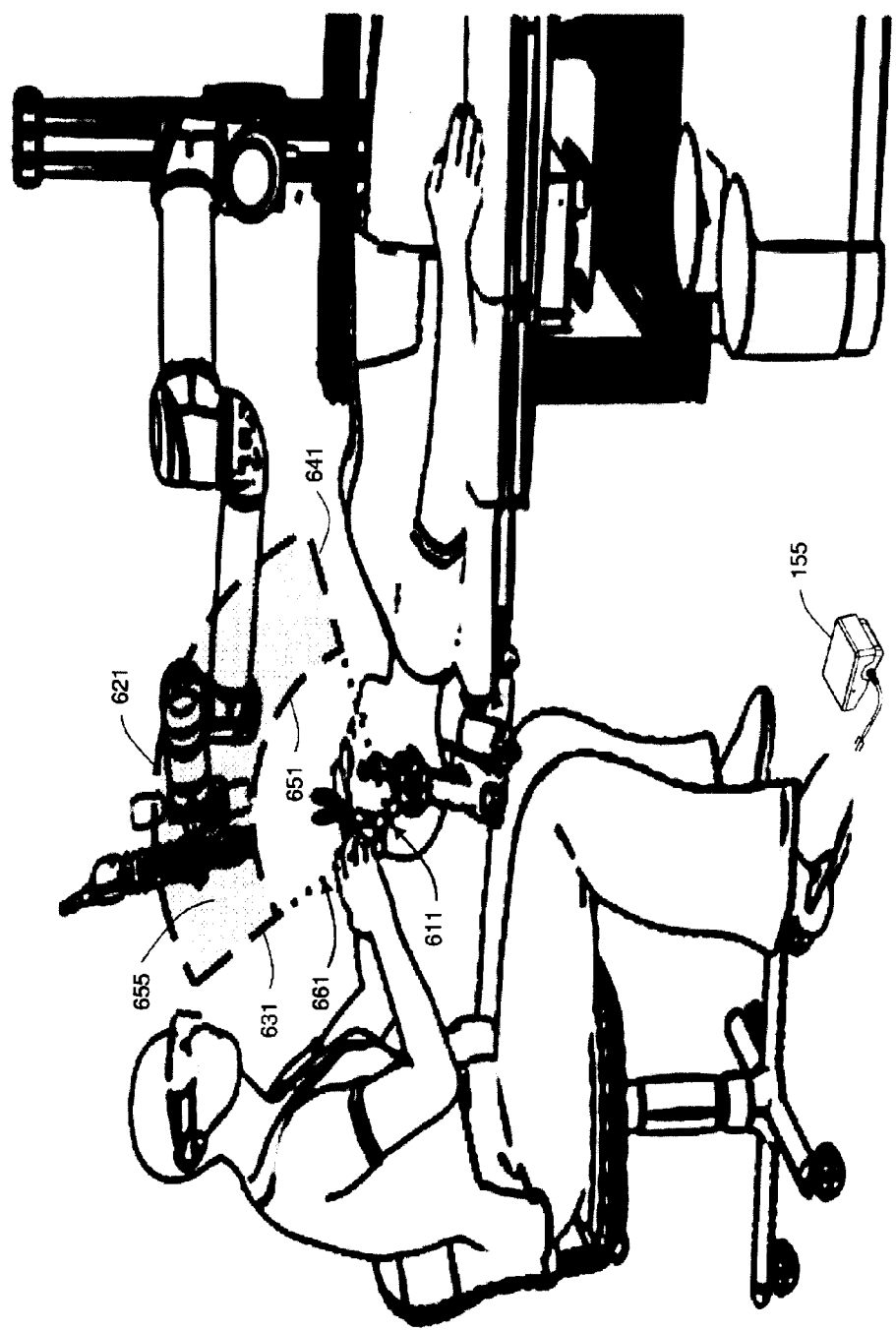

In an alternate embodiment the protective dome may be realized in a virtual manner using proximity sensors. Hence, a physical dome may be absent but a safety zone 655 around the distal end 408 as shown in FIGS. 6B and 6C may be established. In an embodiment this can be accomplished by using proximity sensor technologies to prevent accidental contact between surgical team members and any moving part of the automated arm with mounted imaging sensor. A further embodiment may include a collision sensor to ensure that the moving automated arm does not collide with any object in the environment. This may be implemented using electrical current sensors, force or velocity sensors and/or defined spatial limits of the automated arm.

It should be noted that the safety systems described above are exemplary embodiments of various safety systems that can be utilized in accordance with the intelligent positioning system and should not be interpreted as limiting the scope of this disclosure. In an embodiment the intelligent positioning system is able to acquire the spatial position and pose of the target as well as the automated arm as described above. Having this information the intelligent positioning system can be imposed with a constraint to not position the automated arm within a safety semicircle around the target. In an additional embodiment depicted in FIG. 6C a reference marker 611 can be attached to the patient immobilization frame (117) to provide a reference of the spatial position and pose of the head of the patient, in the common coordinate frame, to the intelligent positioning system through tracking mechanisms described above.

Once the position of this reference marker is determined a positional constraint can be imposed on the automated arm effectively defining a "no-fly zone". Given the reference marker 611 has coordinates $$(x_r, y_r, z_r, \alpha_r, \beta_r, \gamma_r)$$

Where the subscript "r" denotes a coordinate of the reference marker and $\alpha, \beta, \gamma$, are the degree of roll, pitch, and yaw of the marker. Then a new reference origin within the common coordinate frame can be defined by assigning the spatial position of the marker to be the origin and the top, left and right sides of the marker (as determined relative to the common coordinate frame by inferring from the acquired roll, pitch, and yaw) to be the z direction, x direction, and y directions relative to the new reference origin within the common coordinate frame. Given that the position of the end effector on the automated arm is defined in spherical coordinates for example $$(r_E, \phi_E, \theta_E)$$

Where the subscript "E" denotes a coordinate of the end effector, a region can be defined in spherical coordinates which can constrain the movement of the end effector to an area 655 outside of which will be defined a "no-fly zone". This can be achieved by defining an angular range and radial range relative to the reference origin which the end effector cannot cross. An example of such a range is shown as follows:

$$r_{min} < r_E < r_{max}$$

$$\phi_{min} < \phi_E < \phi_{max}$$

$$\theta_{min} < \theta_E < \theta_{max}$$

Where the subscripts "min" denotes the minimum coordinate in a particular spherical direction the end effector can occupy and the subscript denotes the maximum coordinate in a particular spherical direction the end effector can occupy. Exemplary radial and angular limit ranges are given for two dimensions as follows and are shown in FIG. 6C as 651 ($r_{min}$) to 621 ($r_{max}$) and 631 ($\phi_{min}$) to 641 ($\phi_{max}$) respectively. This embodiment may also be used to define additional constrained regions for example such as those concerned with conserving line of sight of the surgeon, conserving line of sight of the tracking device with the tracking markers on the end effector, and conserving the area in which the surgeon hands will be utilizing the tools. Referring to the port based surgery described above a common acceptable offset range (for example the dotted line 661 defining the length from the reference marker to the beginning of the "fly-zone" shown in FIG. 6C) of the end effector to the target, to allow the surgeon to work comfortably is 20 cm to 40 cm (i.e. in this $r_{min}$=20 cm and $r_{max}$=40 cm).

In another embodiment, a safety zone may be established around the surgical team and patient using uniquely identifiable tracking markers that are applied to the surgical team and patient. The tracking markers can be limited to the torso or be dispersed over the body of the surgical team but sufficient in number so that an estimate of the entire body of each individual can be reconstructed using these tracking markers. The accuracy of modelling the torso of the surgical team members and the patient can be further improved through the use of tracking markers that are uniquely coded for each individual and through the use of profile information that is known for each individual similar to the way the tracking assemblies identify their corresponding medical instruments to the intelligent positioning system as described above. Such markers will indicate a "no-fly-zone" that shall not be encroached when the end effector 104 is being aligned to the access port by the intelligent positioning system. The safety zone may be also realized by defining such zones prior to initiating the surgical process using a pointing device and capturing its positions using the navigation system.

In another embodiment multiple cameras can be used to visualize the OR in 3D and track the entire automated arm(s) in order to optimize their movement and prevent them from colliding with objects in the OR. Such a system capable of this is described by the paper [System Concept for Collision-Free Robot Assisted Surgery Using Real-Time Sensing". Jörg Raczkowsky, Philip Nicolai, Björn Hein, and Heinz Wörn. IAS 2, volume 194 of Advances in Intelligent Systems and Computing, page 165-173. Springer, (2012)]

Additional constraints on the intelligent positioning system used in a surgical procedure include self-collision avoidance and singularity prevention of the automated arm which will be explained further as follows. The self-collision avoidance can be implemented given the kinematics and sizes of the arm and payload are known to the intelligent positioning system. Therefore it can monitor the joint level encoders to determine if the arm is about to collide with itself. If a collision is imminent, then intelligent positioning system implements a movement restriction on the automated arm and all non-inertial motion is ceased.

In an exemplary embodiment given an automated arm with 6 degrees of freedom, the arm is unable to overcome a singularity. As such when a singularity condition is approached the intelligent positioning system implements a movement restriction on the automated arm and all non-inertial motion is ceased. In another exemplary embodiment such as that shown in FIG. 5A an automated arm with six degrees of freedom is provided another degree of freedom by the addition of a lifting column 115. In this case singularities can be overcome as the restricted motion in one joint can be overcome with the movement of another joint. Although this allows the intelligent positioning system to overcome singularities it is a more difficult kinematics problem. An end-effector pose is defined by 3 translational and 3 rotational degrees of freedom; to do the inverse kinematics of a 7DOF manipulator requires that you invert a 6×7 matrix, which is not unique. Therefore, while a 7 degree of freedom manipulator allows you to get around singularities due to this non-uniqueness, it is at an additional computational cost. By adding an extra constraint, like the elbow constrained to stay at a particular height, the system would allow a unique solution to be found which would again ease the computational requirement of the system.

Having the automated arm be mobile for medical flexibility and economic viability, instills another constraint on the intelligent positioning system. This is to ensure either the mobile base 512 is in motion or the automated arm is in motion at any given time. This is accomplished by the system by having an auto-locking mechanism which applies breaks to the base when movement of the arm is required. The reasoning for this constraint is movement of the arm without a static base will result in synonymous motion of the base (basic physics). If the arm is mounted on a vertical lifting column, the lifting column adds to this constraint set: the lifting column cannot be activated if the mobile base wheels are not braked or if the arm is in motion. Similarly, the arm cannot be moved if the lifting column is active. If the mobile base wheel brakes are released, the arm and lifting column are both disabled and placed in a braked state.

Advantages of Arm

Figure 8A:
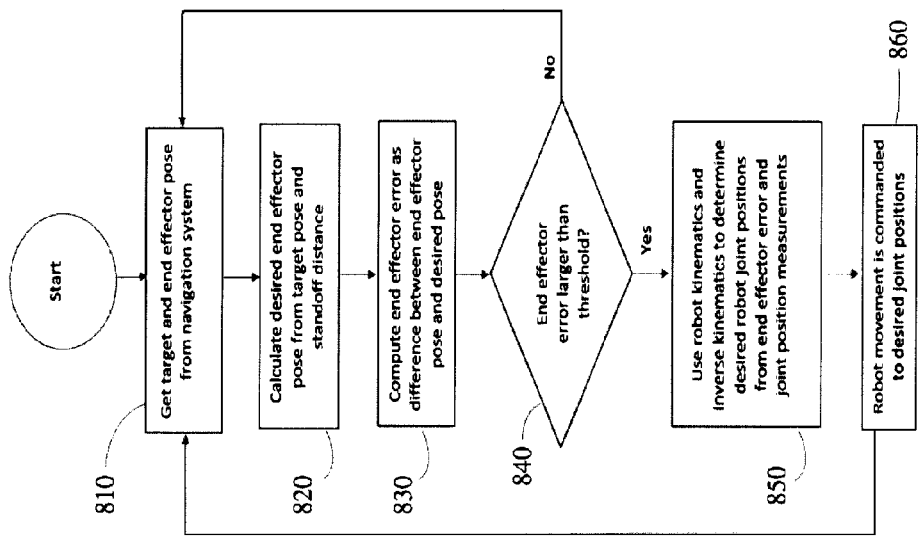
FIG. 8A is a flow chart describing the sequence involved in aligning an automated arm with a target.

In an advantageous embodiment of the system, the automated arm with mounted external scope will automatically move into the zero position (i.e. the predetermined spatial position and pose) relative to the port (target) by the process shown in FIG. 8A. When this is done during the surgical procedure it is possible to start immediately on the treatment of the patient allowing the surgeon to skip the periodic manual step of realigning the external scope with the port.

In the preferred embodiment the chosen position of the automated arm will align the distal end with mounted external scope, to provide the view of the bottom (distal end) of the port (for port based surgery as described above). The distal end of the port is where the surgical instruments will be operating and thus where the surgical region of interest is located. In another embodiment this alignment (to provide the view at the bottom of the port) can be either manually set by the surgeon or automatically set by the system depending on the surgeons' preference and is termed the "zero position". To automatically set the view, the intelligent positioning system will have a predefined alignment for the end effector relative to the port which it will use to align automated arm.

Referring to FIG. 6A which depicts the preferred zero position of the end effector 104 with respect to the port 100. The relative pose of the imaging device (either the external scope 521 or wide field camera 256) is selected such that it guarantees both a coaxial alignment and an offset 675 from the proximal end of the port as shown in both FIGS. 6A-B. More specifically, there ensues a co-axial alignment of the imaging device axis forming, for example, a central longitudinal axis of the imaging device with the longitudinal axis of the port (target) (such as 675 shown in FIGS. 6A-B) as predefined by the zero position. This is particularly suitable for cases such as the port based surgery method mentioned above for tumor resection, as well as Lumbar Microscopic Discectomy and Decompression as it allows the port to be viewed from the optimal angle resulting in the largest field of view for the surgeon, where the surgeon will be manipulating their surgical instruments to perform the surgery. For example, as is described above and illustrated in FIGS. 16A, 16B, and 16C. A co-linear alignment would provide the optimal view given the imaging devices' line of sight is normal to the plane of the region of interest, preventing occlusion by the ports walls which would occur in alternate lines of sight.

Manual/Semi-Manual Automated Arms

The example embodiment of the automated arms shown in FIGS. 6A and 6B and described in the prior paragraph, are shown supporting an external imaging device having tracking markers 246 attached thereto. In these figures, a floor mounted arm is shown with a large range manipulator component 685 that positions the end effector of the automated arm (for example, with 6 degrees of freedom), and has a smaller range of motion for the positioning system (for example, with 6 degrees of freedom) mounted on distal end 408. As shown in FIG. 6A, the distal end of the automated arm 408 refers to the mechanism provided at the distal portion of the automated arm, which can support one or more end effectors 104 (e.g. imaging sensor). The choice of end effector would be dependent on the surgery being performed.

Alignment of the end effector of the automated arm is demonstrated in FIGS. 6A-B. When the access port is moved, the system detects the motion and responsively repositions the fine position of the automated arm to be co-axial 675 with the access port 100, as shown in FIG. 6B. In a further embodiment, the automated arm may maneuver through an arch to define a view that depicts 3D imaging. There are 2 ways to do this—1) is to use two 2D detectors at known positions on the arm, or use one 2D detector and rock back and forth in the view (or move in and out).

Alignment

Figure 7:
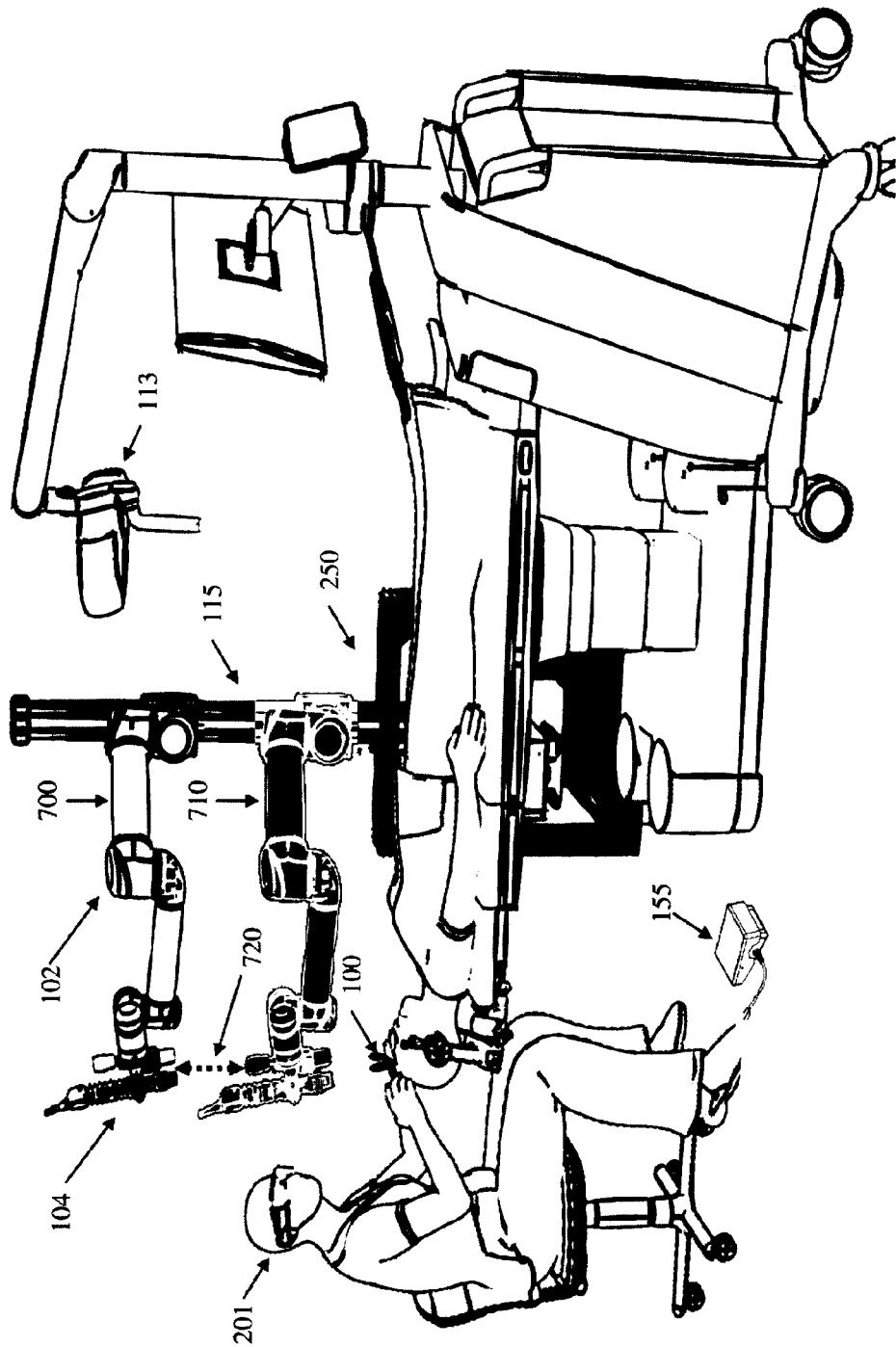
FIG. 7 is an exemplary embodiment of an alignment sequence implemented by the intelligent positioning system.

FIG. 7 is a representation of an alignment sequence implemented by the intelligent positioning system. In FIG. 7, the automated arm 102 may be moved from its actual position 700 into its desired position 710 with the aid of a cost minimization algorithm or equivalently an error minimization method by the intelligent positioning system 250.

In FIG. 7, the the actual position 700 of the automated arm 102 is acquired continually. The automated arm achieves the desired alignment (zero position) with the target (port 100) through movement actuated by the intelligent positioning system. The intelligent positioning system 250 requires the actual position 700 of the arm 102 to approximate the desired position of the arm 710 as depicted by arrow 720 in FIG. 7. This approximation occurs until the position of the actual arm alignment approximates that of the desired alignment (zero position) within a given tolerance. At the desired alignment 710, the automated arm 102 mounted with the imaging device 104 is then in the zero position with respect to the target (port 100). The subsequent alignment of the automated arm 102 into the desired position 710 relative to the port 100 may be actuated either continuously or on demand by the surgeon 201 through use of the foot pedal 155.

The cost minimization method applied by the intelligent positioning system is described as follows and depicted in FIG. 8A. In an embodiment visual serving is executed in a manner in which tracking device(s) 113 are used to provide an outer control loop for accurate spatial positioning and pose orientating of the distal end of the automated arm 102. Where imaging device 104 may be attached. The Intelligent positioning system also utilizes this open control loop to compensate for deficiencies and unknowns in the underlying automated control systems, such as encoder inaccuracy.

FIG. 8A is an exemplary flow chart describing the sequence involved in aligning an automated arm with a target using a cost minimization method. In the first step (810) the end effectors spatial position and pose is determined, typically in the common coordinate frame, through the use of the tracking device or another method such as the template matching or SIFT techniques described in more detail below. In the next step (820), the desired end effector spatial position and pose is determined with the process 1150 shown in FIG. 11 and described further below.

The pose error of the end effector as utilized in step (830), is calculated as the difference between the present end effector spatial position and pose and the desired end effector spatial position and pose and is shown as arrow distance 720 in FIG. 7. An error threshold as utilized in step (840) is determined from either the pose error requirements of the end effector or the automated arm limitations. Pose error may include resolution of the joints, minimizing power, or maximizing life expectancy of the motors. If the pose error of the end effector is below the threshold, then no automated arm movement is commanded and the intelligent positioning system waits for the next pose estimation cycle. If the pose error is greater than the threshold the flow chart continues to step (850) where the end effector error 720 is determined by the intelligent positioning system as a desired movement.

The final step (860) requires the intelligent positioning system to calculate the required motion of each joint of the automated arm 102 and command these movements. The system then repeats the loop and continuously takes new pose estimations from the intelligent positioning system 250 to update the error estimation of the end effector spatial position and pose.

Alignment Flow Chart

Figure 8B:
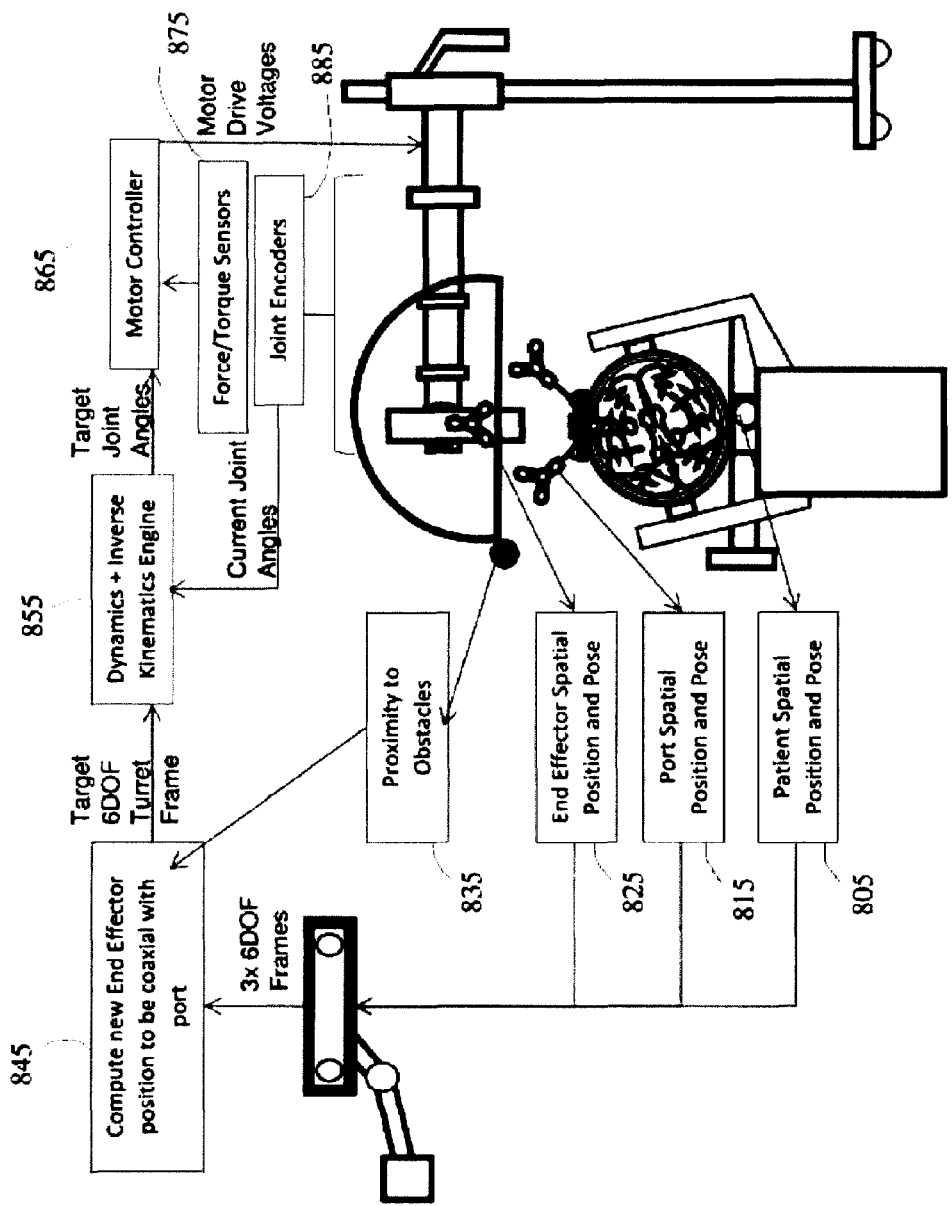
FIG. 8B is a flow chart describing the sequence involved in aligning an automated arm with a target.
Figure 10B:
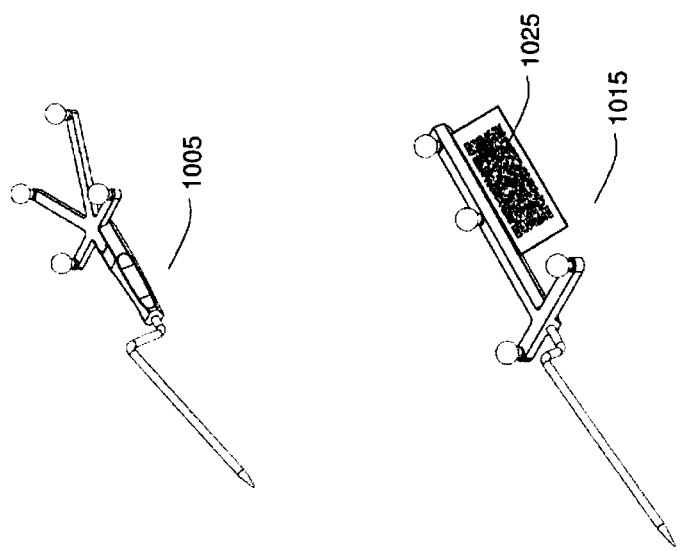

In an embodiment the intelligent positioning system can perform the alignment of the automated arm relative to the port optimized for port based surgery using the method as described by the flow chart depicted in FIG. 8B. FIG. 8B describes the method implemented in the flow chart in FIG. 8A in a refined version as used in the port based surgery described above. In FIG. 8B, an exemplary system diagram is shown illustrating various component interactions for tracking of the access port (target) by the automated arm supporting an imaging device. Tracking and alignment may be triggered manually by the surgeon, or set to track continuously or various other types of automated arm alignment modes as described below in further detail. In both given example modes, the operational flow may be performed as follows:

1. The tracking device(s) transmits the spatial positions and poses of the access port patient and end effector, analogous to step 810 in FIG. 8A, to the intelligent positioning system after which they are registered to the common coordinate frame. The coordinates in this step are given for the port, the patient, and the end effector as 815, 805, and 825 as shown in FIG. 8B respectively.
2. If, for example, the imaging sensor is to be continuously (i.e. in real time) aligned relative to the access port at the zero position as described below (in the common coordinate frame), a new desired spatial position and pose for the end effector (mounted with the imaging sensor) including the zoom, and focus of the camera is calculated which is shown as step (845) in FIG. 8B and is analogous to 820 in FIG. 8A, as described above. In an embodiment the zero position is one that will orient the imaging device coaxially with the access port during a port based surgery as described in more detail below in the description of FIG. 15. If, alternatively, the end effector is continuously aligned relative to a medical instrument for example the surgical pointer tools 1015 and 1005 as shown in FIG. 10B, the same calculations are computed to orient the imaging sensor such that the focal point is aimed at the tip of the medical instrument or aligned relative to it in a predetermined (by the process described in FIG. 11) zero position.
3. In the next step (855), analogous to step 850 in FIG. 8A, of the process the intelligent positioning system (using an inverse kinematics engine) reads the current joint positions of the automated arm and computes offset joint positions for the automated arm that would achieve the desired spatial position and pose of the end effector as defined by the zero position.
4. The intelligent positioning system then drives the joints to the desired joint angles via a motor controller (865) contained in the intelligent positioning system, this step is analogous to step 860 in FIG. 8A. Inputs into the motor controller include the joint encoders (885) located in the automated arm as well as any connected (i.e. to the intelligent positioning system) force/torque sensors 875. It will be understood that various strategies can be used for the determination of the trajectory of the automated arm. Some examples are: straight line path of the distal end frame, equal joint speed, and equal joint travel time. If the location and geometry of other equipment in the vicinity of the arm are known.
5. During the execution of the automated arm trajectory, one or more gauges, sensors or monitors (such as motor current, accelerometers and or force gauges) may be monitored to halt the arm in the case of collision. Other inputs to prevent a collision include proximity sensors that would give information (835) on the proximity of the automated arm relative to obstacles in the automated arms vicinity as well as defined "no-fly zones" 655 depicted in FIGS. 6B-C and described herein.

Because the surgical arena is filled with many pieces of equipment and people, it may be desirable that all gross-alignment of the distal end is performed manually and only the fine adjustment is performed automatically from tracked data.

Constant realignment of an end effector with a moving target during a port based surgery is problematic to achieve as the target is moved often and this can result in increased hazard for the equipment and personnel in the surgical suite. Movement artefacts can also induce motion sickness in the surgeons who constantly view the system. There are multiple embodiments that can deal with such a problem two of which will be described further. The first involves the intelligent positioning system constraining the arm movement so that it only realigns with the target if the target has been in a constant position, different from its initial position, for more than a particular period of time. This would reduce the amount of movement the arm undergoes throughout a surgical procedure as it would restrain the movement of the automated arm to significant and non-accidental movements of the target. Typical duration for maintaining constant position of the target in port based brain surgery is 15 to 25 seconds. This period may vary for other surgical procedures even though the methodology is applicable. Another embodiment may involve estimation of the extent of occlusion of the surgical space due to misalignment of the port relative to the line of sight of the video scope 104. This may be estimated using tracking information available about the orientation of the port and the orientation of the video scope. Alternatively, extent of occlusion of the surgical space may be estimated using extent of the distal end of the port that is still visible through the video scope. An example limit of acceptable occlusion would be 0-30%.

The second embodiment is the actuation mode described herein. Alternate problems with constant realignment of the end effector can be caused by the target as it may not be so steadily placed that it is free of inadvertent minuscule movements that the tracking system will detect. These miniscule movements may cause the automated arm to make small realignments synchronous with small movements of the port. These realignments can be significant as the end effector may be realigning in a radially manner to the port and hence a small movement of the target may be magnified at a stand-off distance (i.e. angular movements of the target at the location of the target may cause large absolute movements of the automated arm located at a radial distance away from the target). A simple way to solve this problem is to have the intelligent positioning system only actuate movement of the arm, if the automated arm's realignment would cause the automated arm to move greater than a threshold amount. For example a movement which was greater than five centimeters in any direction.

Template Matching and Sift Alignment Technique

An alternate method of aligning the port is to use machine vision applications to determine the spatial position and pose of the port from the imaging acquired by the imaging sensor. It should be noted that these techniques (i.e. template matching and SIFT described below) can be used as inputs to step (810) in the flow chart depicted in FIG. 8A and described in detail above, as opposed to the optical tracking devices described above.

The mentioned methods utilize a template matching technique or in an alternate embodiment a SIFT Matching Technique to determine the identity, spatial position, and pose of the target, relative to the end effector mounted on the automated arm. In one embodiment the template matching technique would function by detecting the template located on the target and inferring from its skewed, rotated, translated, and scaled representation in the captured image, its spatial position and pose relative to the imaging sensor.

FIGS. 10A and 10B are illustrations depicting target characteristics that can be utilized in optical detection methods. The FIGS. 10A and 10B contain two targets the first being a surgical pointer tool 1015 and the second being a port 100 both having attached templates 1025 and 1030 respectively. In an alternate detection method the SIFT technique functions by using a known size ratio of two or more recognizable features of a target to analyze an image obtained by an imaging sensor to detect the target. For example as shown in FIG. 10A, the features could be the inner 1020 and outer circumference 1010 contours of the lip of the port 100. Once the feature is identified the SIFT technique uses the features' skewed, rotated, translated, and scaled representation in the analyzed image to infer its spatial position and pose relative to the imaging sensor. Both the SIFT Matching and Template Matching Techniques are described in detail by the paper [Monocular Model-Based 3D Tracking of Rigid Objects: A Survey]. It should be noted that other 3D Tracking methods can be used to determine the identity, spatial position, and pose of a target relative to an imaging sensor through analyzing the imaging obtained by the imaging sensor such as described throughout the mentioned paper [Monocular Model-Based 3D Tracking of Rigid Objects: A Survey, section 4].

Manual/Semi Manual Flow

In further implementations of an intelligent positioning system, both manual and automatic alignment of the automated arm may be achieved using the same mechanism through use of force-sensing joints in the automated arm that would help identify intended direction of motion as indicated by the user (most likely the surgeon and surgical team). The force sensors embedded in the joints can sense the intended direction (e.g. pull or push by the user (i.e. surgical team or surgeon)) and then appropriately energize the actuators attached to the joints to assist in the movement. This will have the distal end moved using powered movement of the joints guided by manual indication of intended direction by the user.

In a further implementation, the spatial position and pose of the distal end or equivalently the mounted external device may be aligned in two stages. The two alignment stages of the present example implementation include 1) gross alignment that may be performed by the user; 2a) fine positioning that may be performed by the user and assisted by the intelligent positioning system; and/or 2b) fine positioning that is performed by the intelligent positioning system independently. The smaller range of motion described in steps 2a) and more apparently in 2b) is optionally bordered by a virtual ring or barrier, such that as the system operates to align the distal end, the distal end does not move at such a pace as to injure the surgeon, patient or anyone assisting the surgery. This is achieved by constraining the motion of the automated arm to within that small ring or barrier. The ring or barrier may represent the extent of the smaller range of motion of the automated arm controlled by the intelligent positioning system.

In further embodiments, the user may override this range and the system may re-center on a new location through step 1 as described above, if the larger range of motion of the automated arm controlled by the intelligent positioning system is also automated.

Figure 9A:
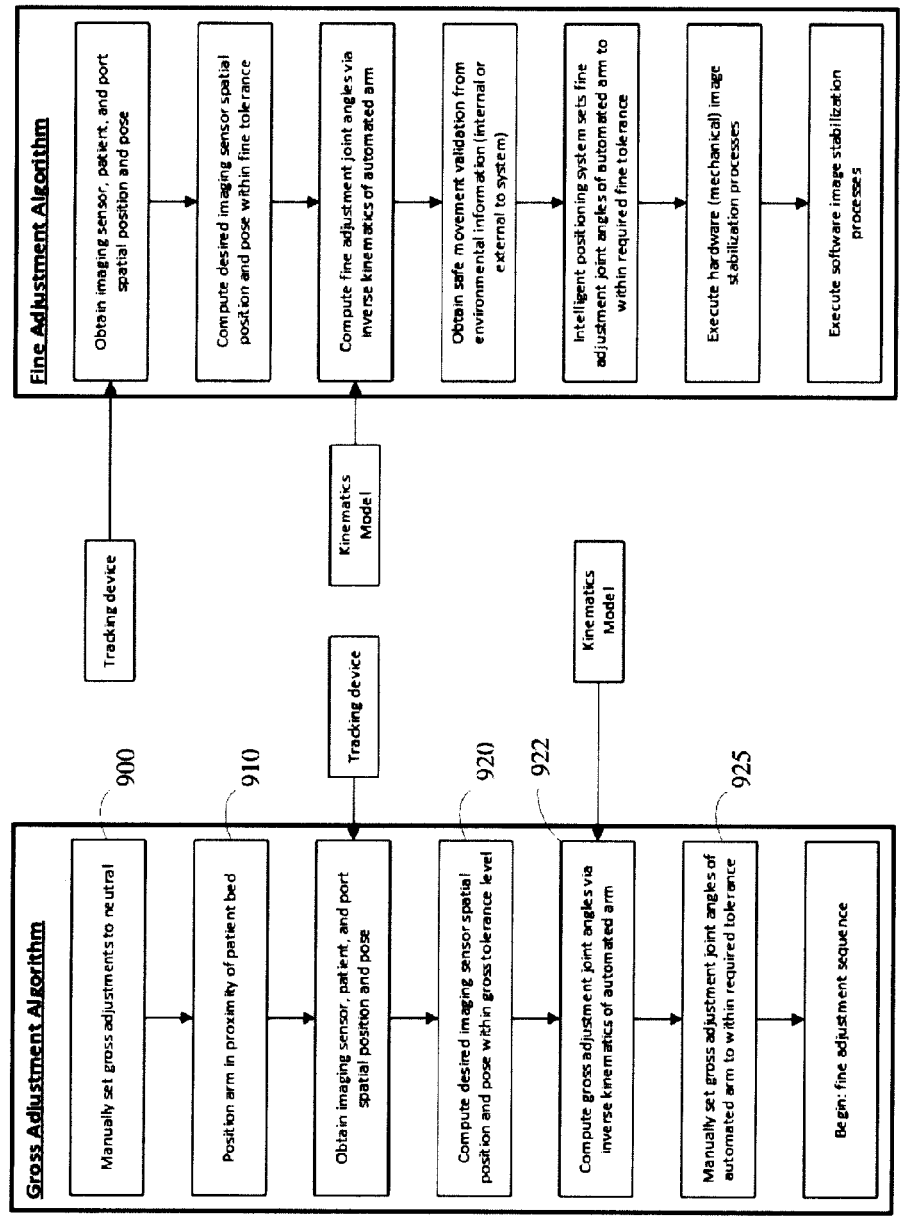
FIG. 9A is a flow chart describing the sequence involved in aligning an automated arm with a target.

An example alignment procedure is illustrated in the flow chart shown in FIG. 9A within the example context of an external imaging device mounted to the automated arm. In this case, a user may initially set the gross alignment joints to a neutral position (900) and wheel it into close proximity of the patient (910). In this position, the intelligent positioning system computes a target end effector spatial position and pose coordinate based on the zero position (920) that will aim the imaging device coaxially (or in another zero position) relative to the access port 100, or, for example, at the tip of a surgical pointer tools 1005 and 1015 shown in FIG. 10B.

In FIG. 9A, the kinematics engine outputs a set of preferred automated arm joint readings to the user that will achieve the zero position within the tolerance achievable by gross alignment (922). The user may then employ these readings to manually perform the initial alignment step (925). In other embodiments, the user may choose to manually adjust the coarse positioning by visual feedback alone, or based on a combination of visual feedback and preferred joint readings. In yet another embodiment, the user may manually perform the initial alignment guided by feedback from the system. For example, the system may provide visual and/or audible information indicating to the user the proximity of the alignment of the system to a pre-selected target range or region of the alignment in the common coordinate frame. The feedback provided may assist the user in identifying a suitable gross alignment, for example, by directing the user's alignment efforts.

In another embodiment, the user may be able to grab the end effector and through a force/torque control loop, guide the end effector into a gross-alignment. This control methodology may also be applied should the surgeon wish to re-orient the external imaging device to be non-coaxial to the access port.

Once the gross alignment is complete, the intelligent positioning system may be employed to perform the fine alignment by moving the automated arm such that the imaging device is brought into the exact zero position via any of the algorithms described above and depicted in FIGS. 8A and 8B. The flow chart shown on the right side of FIG. 9A is another exemplary embodiment describing an automated alignment process which can be executed by the intelligent positioning system again analogous to the flow chart depicted in FIG. 8A.

According to the present embodiments, the alignment of the imaging device is semi-automated; the actions are performed with operator intervention, and feedback from the intelligent positioning system is performed to provide for the fine and/or final alignment of the external device.

During the operator assisted alignment, the spatial position and pose of the imaging device is tracked, for example, by any of the aforementioned tracking methods, such as through image analysis as described above, or by tracking the position of the access port and imaging sensor using reflective markers, also as described above.

The tracked spatial position and pose is employed to provide feedback to the operator during the semi-automated alignment process. A number of example embodiments for providing feedback are presented below. It is to be understood that these embodiments are merely example implementations of feedback methods and that other methods may be employed without departing from the scope of the present embodiment. Furthermore, these and other embodiments may be used in combination or independently.

In one example implementation, haptic feedback may be provided on the automated arm to help manual positioning of the external device for improved alignment. Where an example of haptic feedback is providing a tactile click on the automated arm to indicate the position of optimal alignment. In another example, haptic feedback can be provided via magnetic or motorized breaks that increase movement resistance when the automated arm is near the desired orientation.

In another embodiment, a small range of motion can be driven through, for example magnets or motors, which can drive the spatial position and pose of the external device into desired alignment when it is manually positioned to a point near the optimal position. This enables general manual positioning with automated fine adjustment.

Another example implementation of providing feedback includes providing an audible, tactile or visual signal that changes relative to the distance to optimal positioning of the access port. For example, two audible signals may be provided that are offset in time relative to the distance from optimal position. As the imaging sensor is moved towards optimal position the signals are perceived to converge. Right at the optimal position a significant perception of convergence is realized. Alternatively, the signal may be periodic in nature, where the frequency of the signal is dependent on the distance from the desired position. It is noted that human auditory acuity is incredibly sensitive and can be used to discriminate very fine changes. See for example: http://phys.org/news/2013-02-human-fourier-uncertainty-principle.html.

Figure 9B:
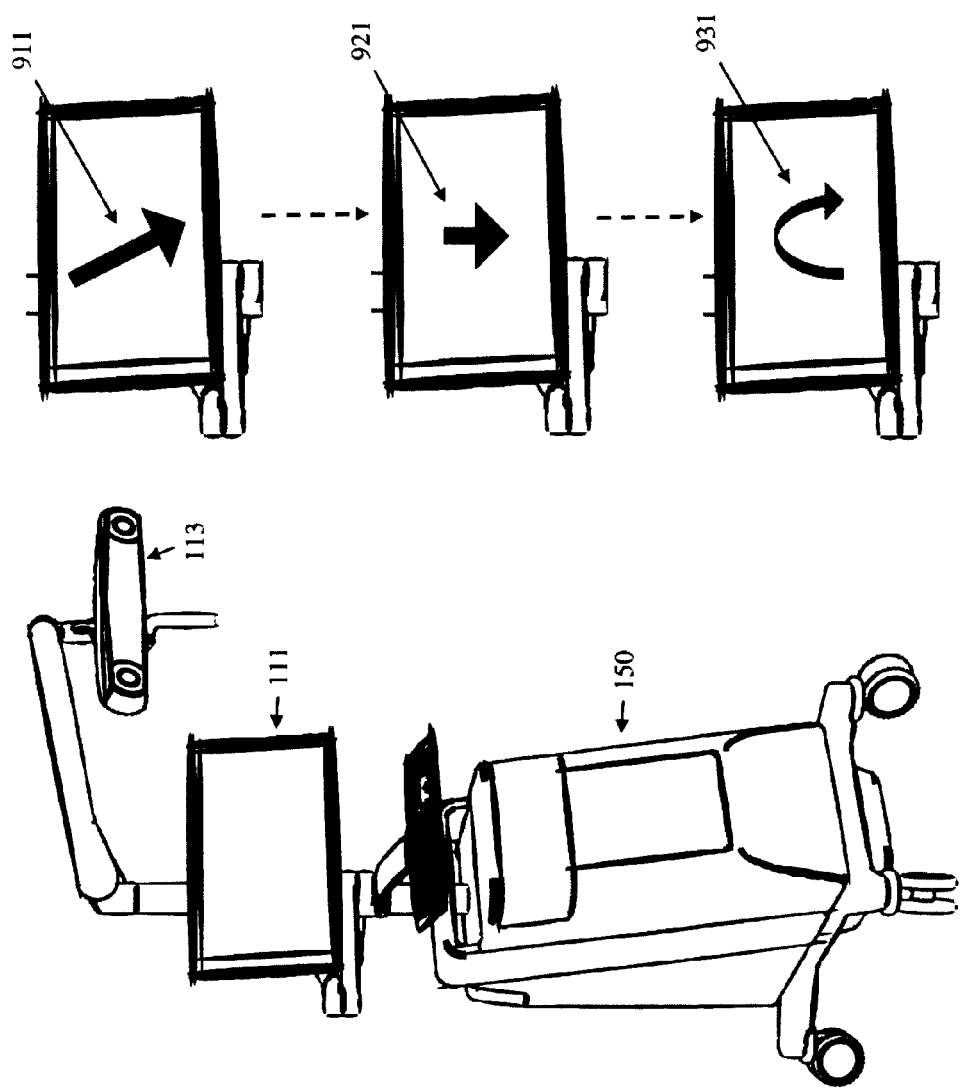
FIG. 9B an illustration depicting a visual cue system for assisting a user in manually aligning an automated arm.

In another example implementation, visual indicators may be provided indicating the direction and amount of movement required to move the imaging sensor into alignment. For example, this can be implemented using light sources such as LEDs positioned on the automated arm, or, for example, a vector indicator on the video display screen of the camera. An example illustration of the vector indicator is shown in FIG. 9B where the arrows 911, 921 and 931 represent visual indicators to the user performing the manual movement. In this figure a shorter arrow 921 represents the spatial position and pose of the imaging device being closer to its required position compared to the longer arrow shown in 911.

Zero Positioning

In an embodiment steps may be taken to set the relative spatial position and pose of the automated arm (mounted with external device or equivalently an imaging device) with respect to the target in the common coordinate frame. for example, that of manually placing the imaging sensor in a chosen spatial position and pose relative to the target spatial position and pose and defining this position to the intelligent positioning system as a zero (chosen) position relative to the port. Which the imaging sensor and accordingly the automated arm should constantly return to, when prompted by the surgeon or automatically by the intelligent positioning system.

Figure 11:
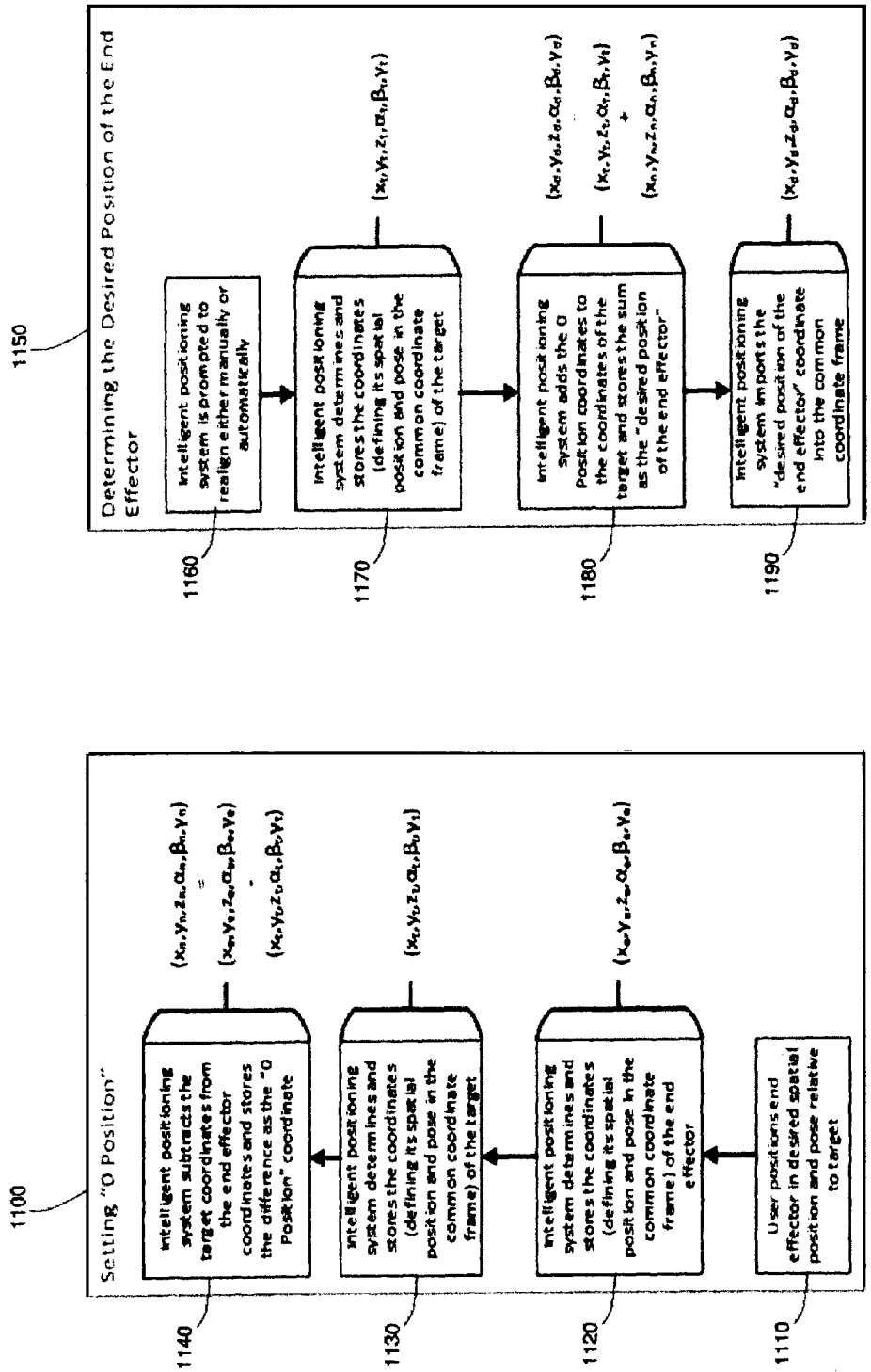
FIG. 11 is a flow chart describing the sequence involved in an embodiment for determining the zero position and desired position of the end effector.

An exemplary embodiment to set the zero position and determine the desired spatial position and pose of the end effector relative to the target are shown in the flow charts in FIG. 11. The left flow chart 1100 describes how to set the zero position and is described further as follows. The first step 1110 is to position the end effector relative to the target in the desired spatial position and pose (manually). Once this is completed the intelligent positioning system moves to the next step 1120 where it acquires the spatial position and pose of the end effector in the common coordinate frame. In the same step it stores this spatial position and pose as coordinates in the common coordinate frame, for example, shown as follows;

$$(x_e, y_e, z_e, \alpha_e, \beta_e, \gamma_e)$$

Where the subscript "e" denotes the coordinates of the end effector and the variables $\alpha$, $\beta$, and $\gamma$ represent roll, pitch, and yaw respectively. The next step 1130 is the same as the prior step 1120 only that the process is applied to the target. Example coordinates acquired for this step are shown as follows;

$$(x_t, y_t, z_t, \alpha_t, \beta_t, \gamma_t)$$

Where the subscript "t" denotes the coordinates of the target. The final step 1140 in the flow chart is to subtract the target coordinates from the end effector coordinates to obtain the "Zero Position" coordinates. The "Zero Position" coordinates is a transform that when added to the dynamic target coordinates during surgery can reproduce the relative position of the end effector to the target in the zero position. An example of this calculation is shown as follows;

$$(x_n, y_n, z_n, \alpha_n, \beta_n, \gamma_n)(x_e, y_e, z_e, \alpha_e, \beta_e, \gamma_e) - (x_t, y_t, z_t, \alpha_t, \beta_t, \gamma_t)$$

Where the subscript "n" denotes the "Zero Position" coordinates.

The right most flow chart 1150 in FIG. 11 describes an example of how the intelligent positioning system determines the desired position of the end effector during a surgical procedure and using the "Zero Position" coordinate. The first step 1160 is to prompt the intelligent positioning system to realign the end effector in the zero position. The next step 1170 is to acquire the spatial position and pose of the target in the common coordinate frame. In the same step it stores this spatial position and pose as coordinates, for example shown as follows;

$$(x_t, y_t, z_t, \alpha_t, \beta_t, \gamma_t)$$

The following step 1180 is to add the "Zero Position" coordinates to the target coordinates to obtain the "desired position of the end effector" coordinates. For example as shown as follows;

$$(x_d, y_d, z_d, \alpha_d, \beta_d, \gamma_d)(x_t, y_t, z_t, \alpha_t, \beta_t, \gamma_t) + (x_n, y_n, z_n, \alpha_n, \beta_n, \gamma_n)$$

Where the subscript "d" denotes the "desired position of the end effector" coordinates. The final step 1190 is to import these coordinates into the common coordinate frame to define to the desired end effector spatial position and pose.

Manual Port Alignment

During an access port procedure, aligning the orientation of the access port for insertion, and ensuring the access port remains in alignment through the cannulation step (as described in more detail below) can be a crucial part of a successful procedure. Current navigation systems provide a display to facilitate this alignment. Some navigation systems are designed to only ensure alignment to the surgical area of interest point regardless of trajectory, while others ensure alignment of a specific trajectory to surgical area of interest point. In any case, this information is displayed on the navigation screen, detached from the view of the actual medical instrument the surgeon is manipulating. With these systems it is often necessary to have a second operator focus on the screen and manually call out distance and orientation information to the surgeon while the surgeon looks at the instrument he is manipulating.

In some embodiments, an alignment device is rigidly and removably connected to the access port, and may also be employed as an alignment mechanism for use during video-based alignment.

Figure 12A:
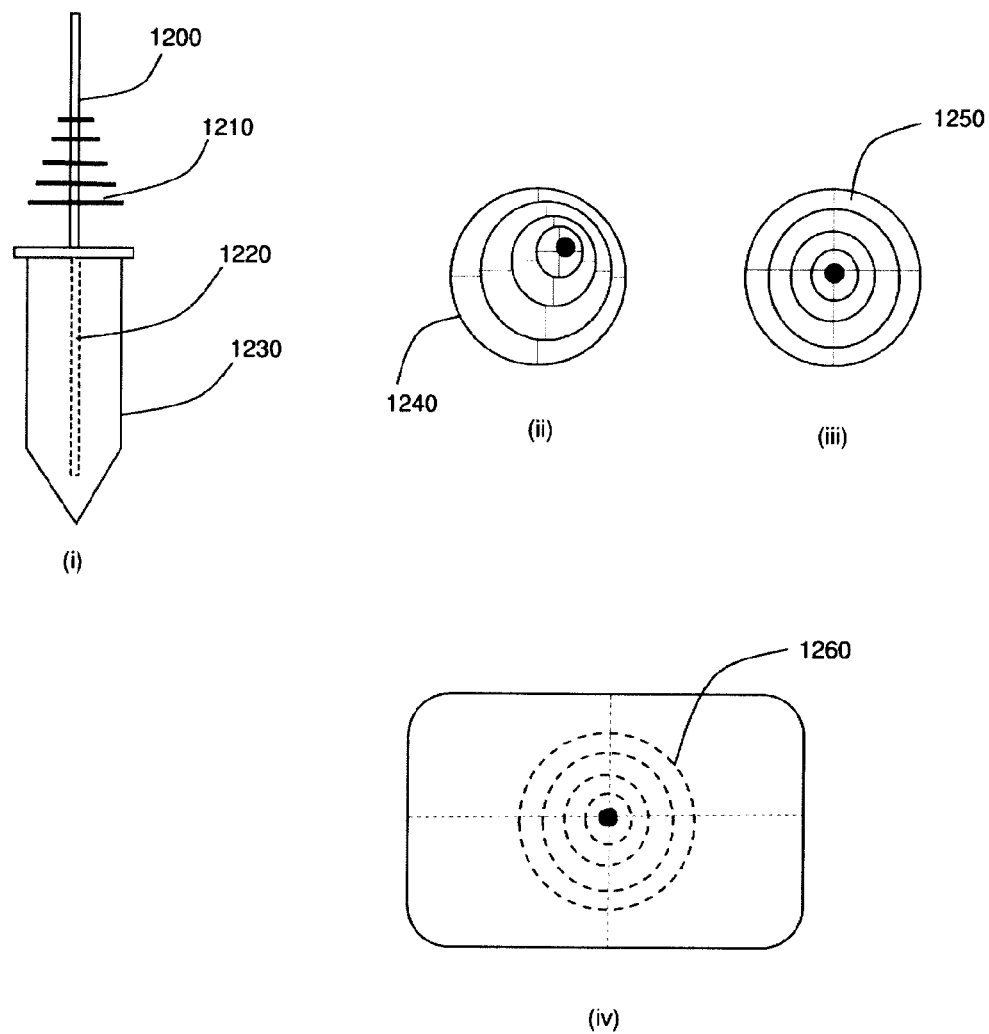
FIG. 12A-B are exemplary embodiments illustration alignment of an access port in multiple views.
Figure 12B:
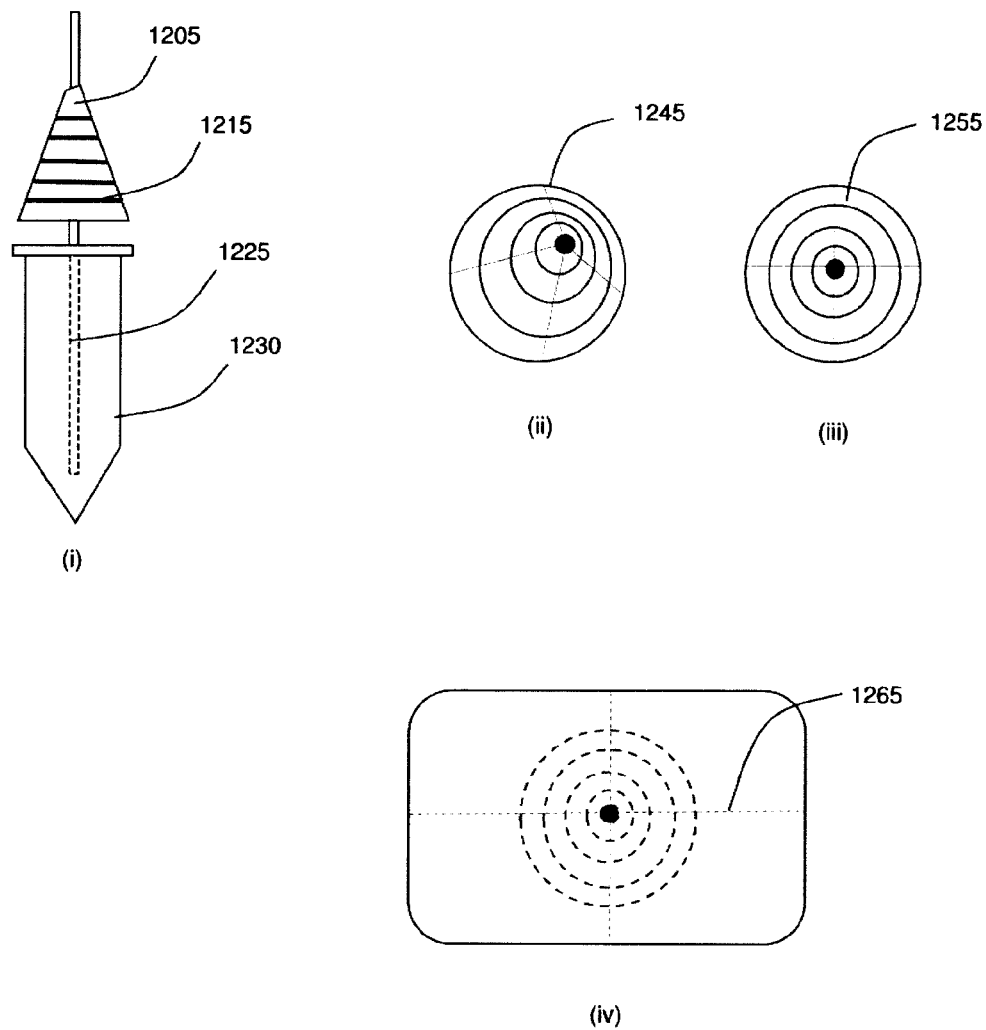

FIG. 12B illustrates an example implementation for aligning an access port based on visual feedback in imaging provided by an external imaging device aligned with the desired trajectory of interest. Conical device 1205 is rigidly and removably attached to access port 1230 with its tip 1225 aligned along the axis of the access port with circular annotations 1215 printed at various depths. When the access port is viewed using an external imaging device with the axis of the external imaging device aligned along the intended insertion path, the circular markers 1215 will appear concentric as shown in FIG. 12B (iii) and (iv). A misaligned access port will result in the circular markers not appearing in concentric fashion. An example of such misalignment is shown in FIG. 12B (ii). Further, a virtual cross-hair 1265 may be displayed on a screen to aid a surgeon to coaxially align the access port while viewing the access port through an externally positioned imaging device. The position of the virtual cross-hair can be based on pre-operative surgical planning and can be the optimal path for inserting the surgical access port for minimizing trauma to the patient.

FIG. 12A illustrates another example implementation in which two or more alignment markers 1210 are provided at different depths along the axis of the access port 1230, optionally with a cross on each alignment marker. These alignment markers can be provided with increasing diameter as the distance increases relative to the imaging device, so that the alignment markers are visible even if partially occluded by nearer alignment markers. In this embodiment, the correct alignment would be indicated by an alignment of all the markers within the annotated representation of the markers, as shown in see FIG. 12A (iii) and (iv).

In one example embodiment, the alignment markers can be provided with a colored edge 1240 that if visible on the imaging device feed, would indicate that the alignment is off axis, as shown in FIG. 12A (ii). The video overlay may also include a display of the depth to the target plane so that the insertion distance can be seen by the surgeon on the same screen as the targeting overlay and the video display of the surgical field.

Modes of Function

In a preferred embodiment the automated arm of the intelligent positioning system will function in various modes as determined but not limited by the surgeon, the system, the phase of surgery, the image acquisition modality being employed, the state of the system, the type of surgery being done (e.g. Port based, open surgery, etc.), the safety system. Further the automated arm may function in a plurality of modes which may include following mode, instrument tracking mode, cannulation mode, optimal viewing mode, actual actuation mode, field of view mode, etc.

The following is a brief summary of some of the modes mentioned above:

Following Mode:

In following mode the automated arm will follow the target at the predetermined (chosen) spatial position and pose as the target is manipulated by the surgeon (for example in the manner illustrated in FIGS. 16C-D and described in detail above), either through electronic or physical means. For the case of the port based surgery commonly used for tumor resection as mentioned above, the surgeon will manipulate the port within the patient's brain as they search for tumor tissue 120 to resect. As the port is manipulated the automated arm mounted with the imaging device will move to consistently provide a constant field of view down the port with lighting conditions geared towards tissue differentiation. This mode can be employed with restrictions to assure that no contact of the arm is made with any other instrument or personnel including the surgeon within the operating room by the process described in the description of FIG. 6C. This restriction can be achieved using proximity sensors to detect obstacles or scene analysis of images acquired for the operating room as described below in greater detail. In addition the surgeon can either dictate the chosen (zero position) spatial position and pose of the arm (including the Imaging device) relative to the target or it can be determined automatically by the system itself through image analysis and navigational information.

Some alternate derivative embodiments of following mode may include

In anti-jitter mode the imaging sensor vibration is compensated for, through the use of various methods such as actuation of magnetic lens, stability coils as well as by slowing the movement of the arm. The jitter can be detected using image analysis software and algorithms as available in the industry today. An example of an anti-jitter mechanism is provided in the patent [U.S. Pat. No. 6,628,711 B1: Method and apparatus for compensating for jitter in a digital video image]

In delayed following mode the arm is adjusted to assure the predetermined (zero position) spatial position and pose of the imaging device is kept constant, but the following movement has a delay to reduce the probability of minor undeliberate movements of the target (the port 100 in the case of port based surgery)

Instrument Tracking Mode:

In instrument tracking mode the automated arm can adjust the imaging device to follow the medical instruments used by the surgeon, by either centering the focus or field of view and any combination thereof on one instrument, the other instrument, or both instruments. This can be accomplished by uniquely identifying each tool and modelling them using specific tracking marker orientations as described above.

Cannulation Mode:

In cannulation mode the automated arm adjusts the imaging device to an angle which provides an improved view for cannulation of the brain using a port. This would effectively display a view of the depth of the port and introducer as it is inserted into the brain to the surgeon Optimal Viewing Mode:

Given the images captured by the imaging device an optimal viewing mode can be implemented where an optimal distance can be obtained and used to actuate the automated arm into a better viewing angle or lighting angle to provide maximized field of view, resolution, focus, stability of view, etc. as required by the phase of the surgery or surgeon preference. The determination of these angles and distances within limitations would be provided by a control system within the intelligent positioning system. The control system is able to monitor the light delivery and focus on the required area of interest, given the optical view (imaging provided by the imaging sensor) of the surgical site, it can then use this information in combination with the intelligent positioning system to determine how to adjust the scope to provide the optimal viewing spatial position and pose, which would depend on either the surgeon, the phase of surgery, or the control system itself.

Actuation Mode:

Additional modes would be actuation mode in which case the surgeon has control of the actuation of the automated arm to align the imaging device with the target in a chosen spatial position and pose and at a pre-set distance. In this way the surgeon can utilize the target (If a physical object) as a pointer to align the imaging device in whatever manner they wish (useful for open surgery) to optimize the surgery which they are undertaking.

Field of View Mode:

In field of view mode the automated arm in combination with the imaging device can be made to zoom on a particular area in a field of view of the image displayed on the surgical monitor. The area can be outlined on the display using instruments which would be in the image or through the use of a cursor controlled by a personnel in the operating room or surgeon. Given the surgeon has a means of operating the cursor. Such devices are disclosed in US Patents.

Combination of Modes:

The modes mentioned above and additional modes can be chosen or executed by the surgeon or the system or any combination thereof, for example the instrument tracking mode and optimal lighting mode can be actuated when the surgeon begins to use a particular tool as noted by the system. In addition the lighting and tracking properties of the modes can be adjusted and made to be customized to either each tool in use or the phase of the surgery or any combination thereof. The modes can also be employed individually or in any combination thereof for example the Raman mode in addition to the optical view mode. All of the above modes can be optionally executed with customized safety systems to assure minimization of failures during the intra-operative procedure.

Optimization of View at End of Port

In the context of an imaging device formed as a camera imaging device with a configurable illumination source, supported by the automated arm, alignment with the access port may be important for a number of reasons, such as, the ability to provide uniform light delivery and reception of the signal. In addition, auto-focus of the camera to a known location at the end of the access port may be required or beneficial.

In some implementations, the present embodiments may provide for accurate alignment, light delivery, regional image enhancement and focus for external imaging devices while maintaining an accurate position. Automated alignment and movement may be performed in coordination with tracking of the target (access port). As noted above, this may be accomplished by determining the spatial position and/or pose of the target (access port) by a tracking method as described above, and employing feedback from the tracked spatial position and/or pose of the external imaging device when controlling the relative position and/or pose of the external imaging device using the automated arm.

In an embodiment, directional illumination device such as a laser pointer or collimated light source (or an illumination source associated with an imaging device supported by the automated arm) may be used to project.

Optical Optimization of Port

In yet a further embodiment, a calibration pattern is located at or near the proximal end of the access port. This pattern will allow the camera imaging device to automatically focus, align the orientation of its lens assembly, and optionally balance lighting as well as color according to stored values and individual settings. An exemplary method used to identify the particular type of port being used is the template matching method described above. The template 1030 shown in FIG. 10A, can be used to provide the required information about the port dimensions for optimal lighting and focus parameters that the imaging device can be configured to conform with.

Another stage of alignment may involve the camera imaging device focusing on the tissue deep within the access port, which is positioned at a known depth (given the length of the access port is known and the distance of the port (based on the template on the proximal end of the port). The location of the distal end of the access port 100 will be at a known position relative to the imaging sensor 104 of FIG. 1 and tracked access port 100, in absolute terms, with some small-expected deviation of the surface of the tissue bowing into the access port at the distal end. With a given field of view, camera optical zoom/focus factors, and a known distance from the detector to end of access port, the focus setting can be predetermined in a dynamic manner to enable auto-focus to the end of the tissue based simply on tracking of the access port and camera location, while using some known settings (camera, access port length, focus optics/mechanics, desired field of view). In this manner, a stable focus can be established to maximize the desired field of view.

In a similar, closed-loop manner, color and white balance of the imaging device output can be determined through suitable imaging processing methods. A significant issue with current surgical optics is glare caused by fluids reflecting the intense illumination in the surgical cavity. The glare causes imbalance in the dynamic range of the camera, where the upper range of the detectors dynamic range is saturated. In addition, the illumination intensity across the frequency spectrum can be unbalanced depending on the illumination and surgical conditions. By using a combination of calibration features or targets on the access port (100), and using pre-set parameters associated with the combination of camera and light source, the images can be analyzed to automatically optimize the color balance, white balance, dynamic range and illumination uniformity (spatial uniformity). Several published algorithms may be employed to automatically adjust these image characteristics. For example, the algorithm published by Jun-yan Huo et. al. ("Robust automatic white balance algorithm using gray color points in images," IEEE Transactions on Consumer Electronics, Vol. 52, No. 2, May 2006) may be employed to achieve automatic white balance of the captured video data. In addition, the surgical context can be used to adapt the optimal imaging conditions. This will be discussed in greater detail below.

Two Stage Method Image Optimization

Alternatively, in a two-step approach, the tracking system can be employed, in a first step of alignment, to track the position of the access port, for a gross calculation of spatial position and pose. This allows for an imaging device 104, as seen in FIG. 1, to be positioned in a co-axial manner relative to the port 100, and at the appropriate focal distance and focal setting based on the field of view, resolution, and frame rate, defined by the user. This will only be accurate within the tolerance of the tracking capability of the system, the mechanical positioning accuracy of the automated arm, and the tissue deflection at the tip of the access port.

A second stage alignment, based on imaging optimization and focus, can optionally be achieved by interaction of the imaging sensor, positioning of the automated arm, analysis of the images, and the use of range detection to the end of the access port (for example by template matching), and centered at the distal end of the access port. For example, as is currently done with more traditional auto-focus functions of digital camera systems, the image can be analyzed to determine the sharpness of the image by way of image metric quantification in a series of focal zones. The focal zones would be directed to a location at the end of the access port, where the gross positioning of the system would allow for this fine, and more focused approach to automatically detect the focal zone as being within the field of view of the end of the access port. More specifically, this is defined as a zone smaller than the field of view of the access port.

In addition, one or more range detectors can be used, optionally through the lens of the imaging device 104, so that the actual position of the tissue at the end of the access port can be calculated. This information can be provided as input into the iterative algorithm that determines the optimal imaging device position, and focal settings.

Optimized Illumination and Data

The coaxial alignment of the imaging sensor with the access port, enables efficient light delivery to the end of the access port which is vital to acquiring higher resolution imaging, as well as the ability to focus optics so as to enhance or maximize the detector efficiency. For instance, with a poorly aligned access port and imaging sensor, only a small fraction of the imaging sensor is utilized for imaging of the area of interest, i.e. the end of the access port. Often only 20% of the total detector is used, while a properly aligned imaging sensor can yield 60%+detector efficiency. An improvement from 20% to 60% detector efficiency roughly yields an improved resolution of 3 times. A setting can be established on the system to define a desired efficiency at all times. To achieve this, the intelligent positioning system will actuate the movement of the automated arm, mounted with the imaging sensor, and focus it at the distal end of the access port as it is maneuvered by the surgeon to achieve the desired detector efficiency, or field of view.

Homgenized Light Delivery

Figure 13:
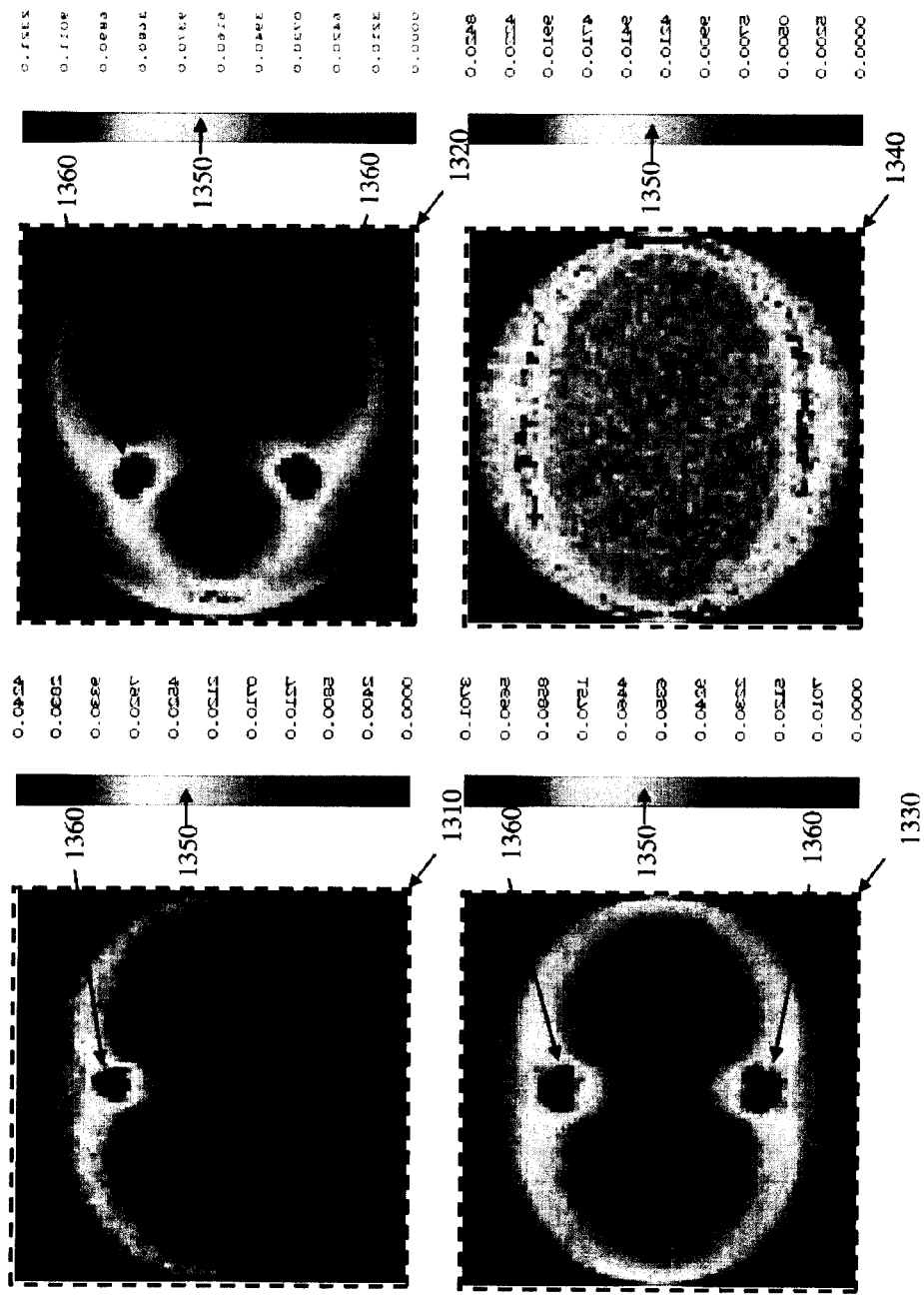
FIG. 13 an illustration depicting port characteristics that can be utilized in optical detection methods.

Another advantageous result of this embodiment is the delivery of homogenized light through the port to the surgical area of interest permitting improved tissue differentiation between healthy and unhealthy brain tissue by potentially reducing glare and reducing shadows which fall on the tissue due to the port. For example the intelligent positioning system can utilize light ray tracing software (such as ZMAX) to model the system given the constraints of the spatial position, pose and 3D virtual model of the port as well as the spatial position, pose and model illumination source as shown in FIG. 13. The first model 1310 shows the illumination of the region of interest using a single illumination element on the external imaging device at a given distance and pose relative to the port. The second 1320 and third 1330 models show illumination of the region of interest using illumination from two sources each. The pairs of sources in each model are oriented differently with respect to the other model. Both models two and three have the same distance and pose parameters as model one relative to the port. The final model 1340 shows illumination from two sources with the same orientation as the sources in the second model 1320 relative to the imaging device, with the same pose but, a different distance. The color map on each region of interest (distal end of the port) shown in the figure describes the illumination level, where mid-range 1350 represents the ideal illumination level.

As can be seen in FIG. 13, hot spots 1360 exist in models one through three (1310, 1320, 1330) which result in heavy glare at those positions and inadequate imaging for the surgeon, while model four 1340 provides the optimal lighting condition (homogenized and low glare delivery of illumination). Using model four as the optimal spatial position and pose alignment of the illumination source, the automated arm would position the imaging sensor (inclusive of the illumination source) to achieve this particular illumination level map thereby improving the view of the surgical area of interest for the surgeon. The software can then determine the optimal spatial position and pose of the illumination source (the Imaging device in this case) relative to the target (port) given the restrictions of the system (minimum offset 575 as shown in FIG. 6A-B) to ensure optimal light delivery through the port to the region of interest. The illumination source may be also optimally positioned after modelling the shadow cast by the surgical tools. In other words, the target region within the field of view may be optimally illuminated while avoiding casting of shadows from the medical instruments utilized by the surgeon within the port. This is possible given the spatial position and pose of the medical instrument can be estimated using tracking markers placed on the surgical tools.

Figure 14A:
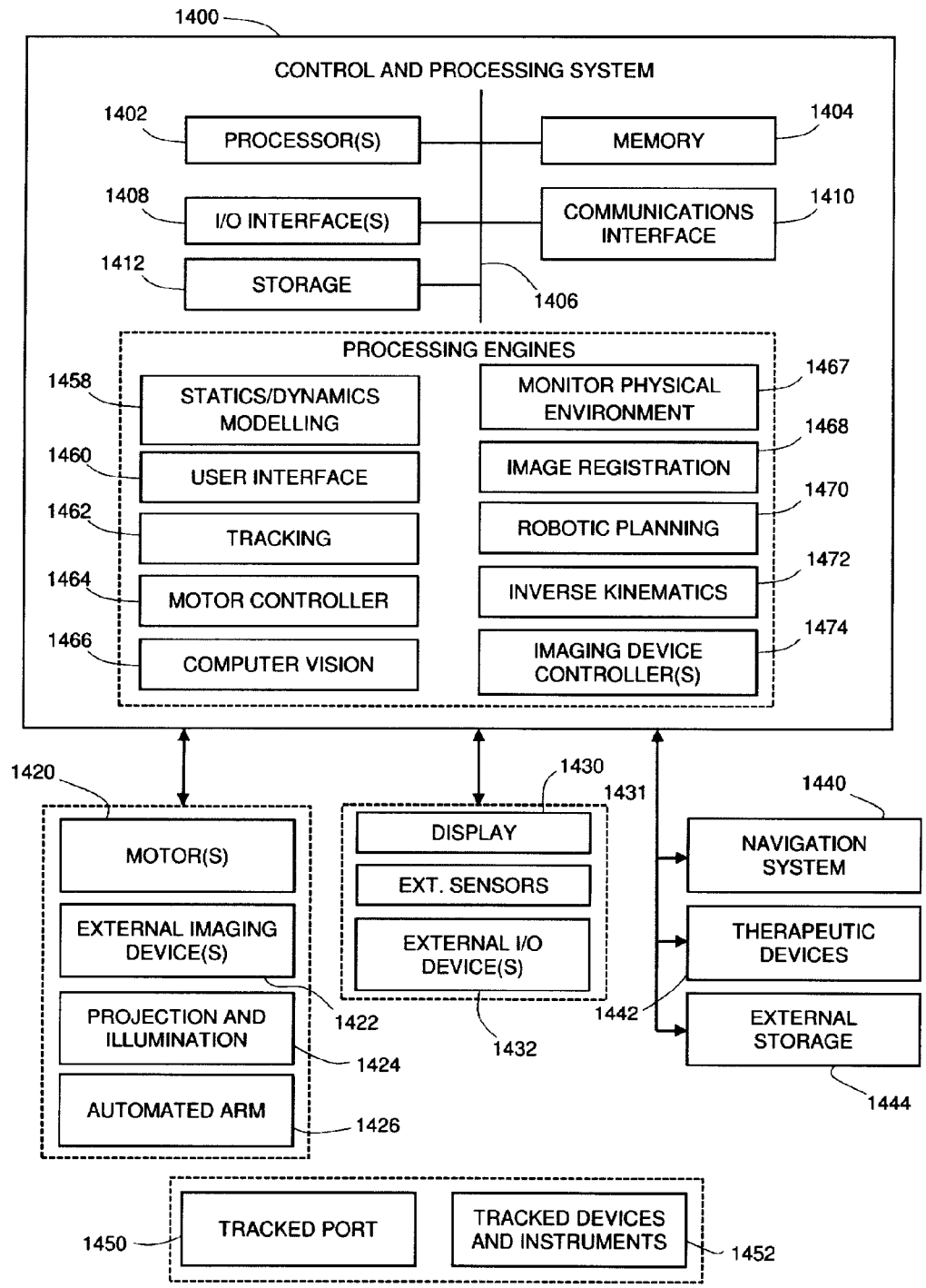
FIG. 14A-B are block diagrams showing an exemplary navigation system including an intelligent positioning system.
Figure 14B:
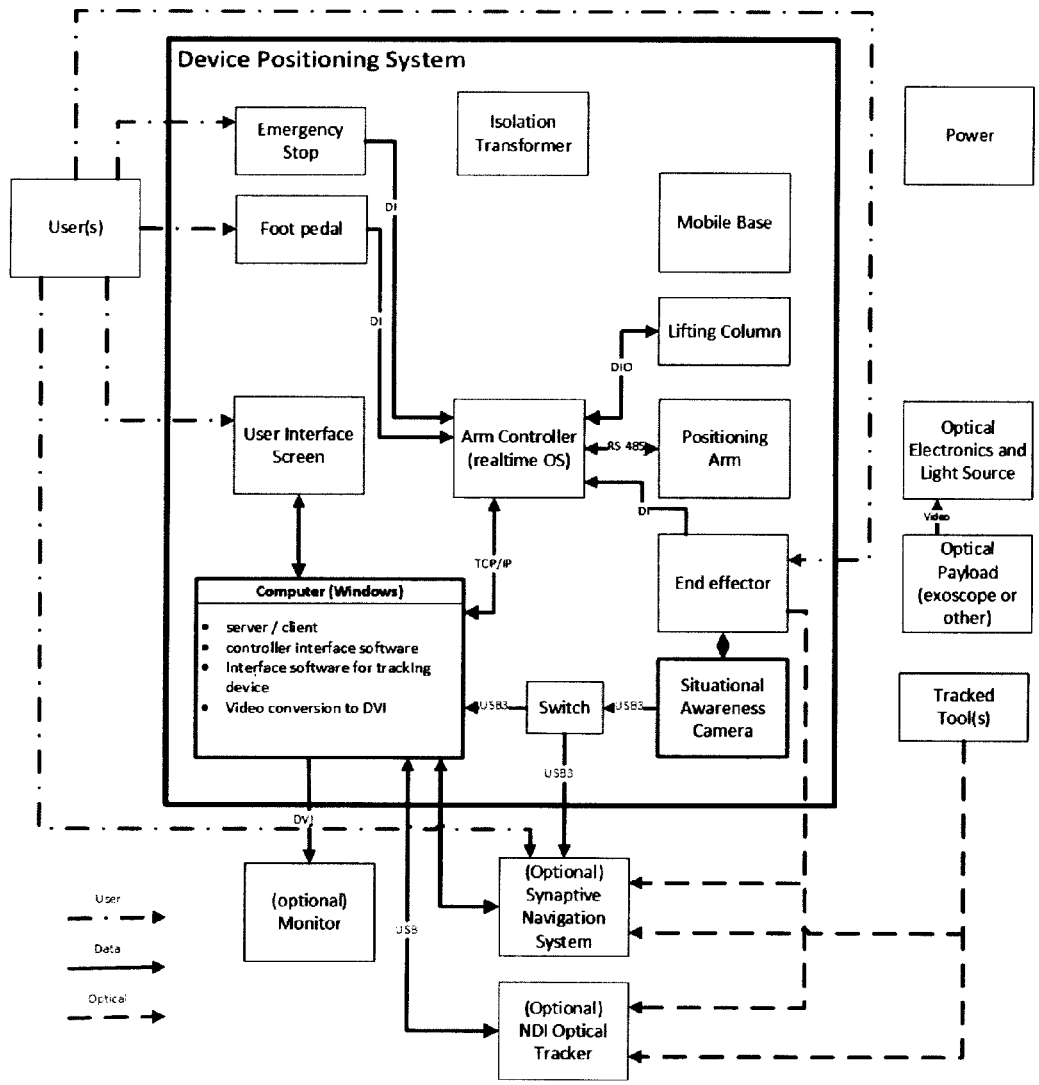

Referring now to FIGS. 14A and 14B, a block diagram of an example system configuration is shown. The example system includes control and processing system 1400 and a number of external components, shown below.

As shown in FIG. 14A, in one embodiment, control processing system 1400 may include one or more processors 1402, a memory 1404, a system bus 1406, one or more input/output interfaces 408, a communications interface 1410, and storage device 1412. Processing and control system 1400 is interfaced with a number of external devices and components, including, for example, those associated with access port imaging and tracking, namely motor(s) 1420, external imaging device(s) 1422, projection and illumination device(s) 1424, and automated arm 1426. External user input and user interface rendering is facilitated by one or more displays 1430 and one or more external input/output devices 1426 (such as, for example, a keyboard, mouse, foot pedal, microphone and speaker).

Processing and control system 1400 is also interfaced with an intelligent positioning system 1440 inclusive of a tracking device 113 for tracking items such as an access port 100 in Figure or 1450 in FIG. 14 and one or more devices or instruments 1452. Additional optional components include one or more therapeutic devices 1442 that may be controlled by processing and control system 1400, and external storage 1444, which may be employed, for example, for storing pre-operative image data, surgical plans, and other information.

It is to be understood that the system is not intended to be limited to the components shown in FIG. 1400. One or more components control and processing 1400 may be provided as an external component that is interfaced to a processing device. In one alternative embodiment, navigation system 1440 may be integrated directly with control and processing system 1400.

Embodiments of the disclosure can be implemented via processor 1402 and/or memory 1404. For example, the functionalities described herein can be partially implemented via hardware logic in processor 1402 and partially using the instructions stored in memory 1404, as one or more processing engines. Example processing engines include, but are not limited to, statics and dynamics modeling engine 1458, user interface engine 1460, tracking engine 1462, motor controller 1464, computer vision engine 1466, engine to monitor surrounding environment of the automated arm based on sensor inputs 1431, image registration engine 1468, robotic planning engine 1470, inverse kinematic engine 1472, and imaging device controllers 1474. These example processing engines are described in further detail below.

Some embodiments may be implemented using processor 1402 without additional instructions stored in memory 1404. Some embodiments may be implemented using the instructions stored in memory 1404 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

It is further noted that in some embodiments, unlike a typical automated arm which has to account for unknown weight of the material picked up by the distal end, automated arm need only account for the known weight of external devices (such as imaging devices) attached to the distal end. Hence, known statics and dynamics of the entire automated arm can be modeled a priori (e.g. via engine 1458 of FIG. 14) and this knowledge can be incorporated in the accurate control of the arm during tracking. Further, imaging and tracking modalities can be used to provide situational awareness for the automated arm, as described above. This situational knowledge can be incorporated during tracking of the access port by the external device or devise supported by the arm to avoid accidental collision of the arm with obstacles in the path such as surgical team, other equipment in the operating room and the patient. This situational awareness may also arrive from proximity sensors optionally mounted on the automated arm and/or distal end, as noted above.

In one embodiment the system is configured consistently with the block diagram shown in FIG. 14B. FIG. 14B is an exemplary embodiment of the intelligent positioning system illustration utilized in connection with a navigation system. The descriptions below outline various exemplary communication paths which may be utilized throughout the intelligent positioning system (IPS).

User->Foot Pedals->Arm Controller->Positioninq Arm

The surgeon has three discrete-input pedals to control the IPS:
1. Align to Tool: Pressing this pedal 155 shown in FIG. 1 will align the scope 266 to the target (such as the port 100) that is currently being tracked. The pedal 155 needs to be continuously held during the motion to the point of the tool at the time the pedal was initially depressed. The user needs to press the pedal again to realign.
2. Increase Standoff: The pedal will increase the standoff distance 675 between the selected tool and the scope. The distal end will move at constant velocity while depressed. The standoff distance can be increased until reach limits of the automated arm are obtained.
3. Decrease Standoff: This pedal decreases the standoff distance 675, at a constant velocity, of the distal end and the selected tool. This motion will cease once a minimum standoff distance is reached (dependent upon scope and tool selected).

These pedals are connected to the digital inputs on the automated arm through the intelligent positioning system 250. The automated arm controller sends joint-level commands to the motor drivers in the automated arm.

These foot-pedals may be enhanced to include Optics control as well.

User->Touch Screen->UI Computer->Arm Controller

The user can interface with the robot through a touch screen monitor. These are generally done prior to surgery.
1. Initialize the joints: As the robot arm only has relative encoders, each joint must be moved up to 20 degrees for the system to determine its absolute position. The UI provides an initialization screen in which the user moves each joint until the encoders are initialized.
2. Selection of imaging sensor: Selection of imaging sensor on the UI computer gets sent to the automated arm controller. The different imaging sensors have different masses, and different desired relative spatial positions and poses relative to the target (for example the port).
3. Selection of tracked medical instrument: Selection of which target to track (given multiple targets, for example a port or a medical instrument or etc.) on the UI computer gets sent to the automated arm controller.
4. Degree of Freedom Selection: The user can select if the tool will be tracked in 6-, 5- or 3-DoF mode.
5. Set 0 position: Set a new spatial position and pose of the automated arm (and consequently the imaging sensor given it is mounted on the automated arm) with respect to a target (for example the port)

NDI Optical Tracker->UI Computer->Arm Controller

The NDI tracking system acquires the distal end (or equivalently the imaging sensor) spatial position and pose within its field of view. It sends this data to the UI Computer which shares the tracked target and distal end information with the automated arm controller so that the spatial position and pose can be calculated. It may also use the patient reference and registration to determine a no-access zone.

Situational Awareness Camera->UI Computer->Monitor

The situational awareness camera (specific embodiment of an imaging sensor) provides imaging of the surgical site. This imaging is sent to the UI computer which turns them into a video stream which is output to an external monitor. As well, the UI computer may overlay warnings, error messages or other information for the user on the video stream.

Phases of Port Based Surgery

Figure 15:
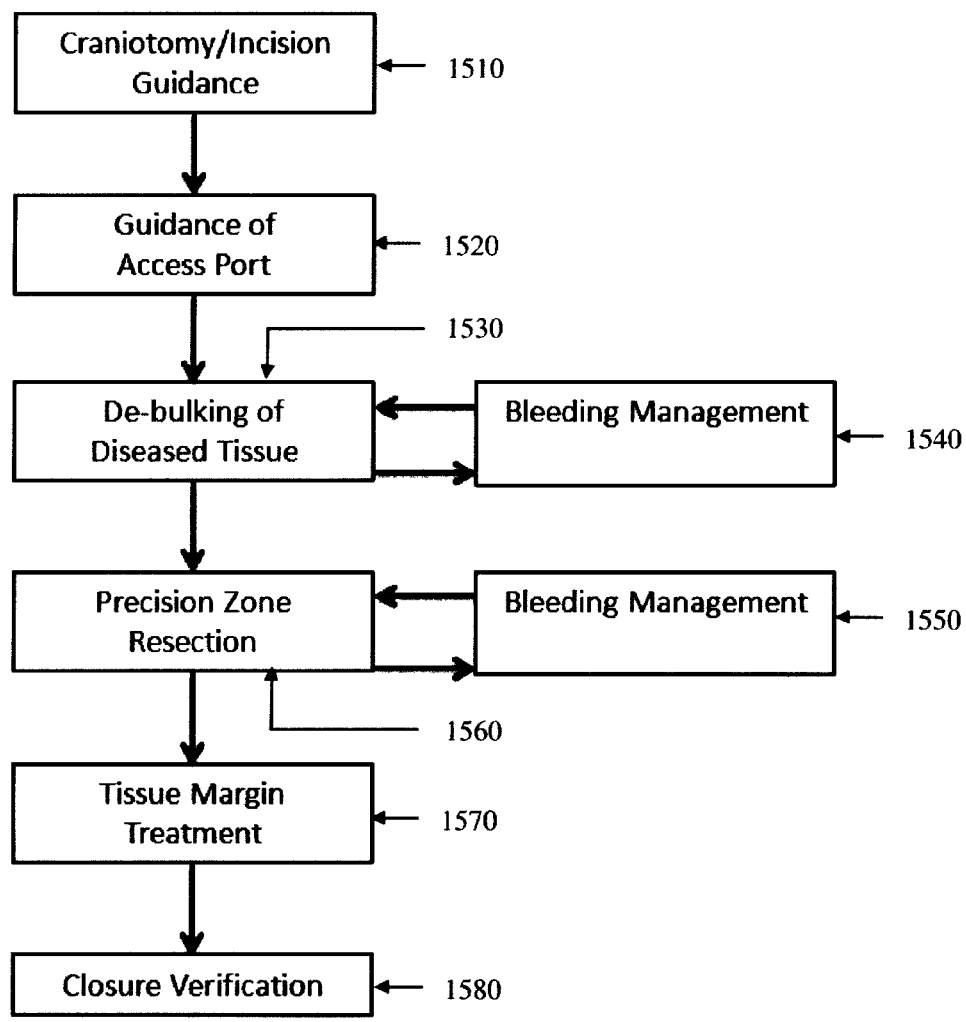
FIG. 15 is a flow chart describing the steps of a port based surgical procedure.

An example phase breakdown of the port based surgical operation is shown in FIG. 15. The arm can be utilized in a corresponding manner to each of the phases to compliment and ease the surgeons process during each step.

The first step (1510) is the incision of the scalp and craniotomy. During these procedures the automated arm (102) (connected to the imaging device (104)) can be implemented to guide the surgeon to the correct position of the craniotomy with respect to the brain within the skull automatically. This is achievable through the use of the navigation system conjointly with the automated arm.

Once the incision and craniotomy are completed the surgery enters the next phase (1520) and the automated arm can be used to perform an US above the dura either automatically by the system or manually by the surgical team. Using this information and input from the intelligent positioning system the automated arm (with mounted imaging device) can project the sulci onto the dura to allow for a better guidance of the dura incision and increased orientation awarness. After the dura incision the cannulation process begins. In this sub-phase the automated arm can be adjusted to an alternate angle to provide a view of the graduation marks on the port whilst its being cannulated into the brain so the surgeon can see its depth.

In the next simultaneous phases (1530 and 1540) the automated automated arm 102 has the most utility as it aids in providing clear images of the distal end of the port for gross de-bulking of unhealthy brain tissue. During this step the surgeon 201 will maneuver the port 100 in the brain of the patient 202 through a multiplicity of motions (for example 1665 in FIG. 16C) to resect the tumor (120), as the distal end of the port in most cases does not provide the access needed to resect the entire tumor in one position an example of this is shown in FIG. 16C as the unaccessible part of the tumor 1680. As the port is maneavuvered the automated arm (with connnected imaging device) can follow the port in a coaxial manner to consistently provide a view of the distal end (for example as shown in FIG. 6A-B) where the surgeons tools (for example (1612)) are operating, an example flow of the constant alignment of the automated automated arm and connected scope is provided in FIG. 8B. This saves the surgeon and surgical team time and streamlines the surgical process by preventing the surgical team from having to constantly readjust the imaging device to view down the port at the correct angle to provide the required surgical view as is required in present surgical systems such as the UniArm Surgical Support System (by Mitaka USA Inc.). This also increases the accuracy of the surgeon by keeping the display of the surgical site in the same direction (relative to brain anatomy or any other reference) resulting in the surgeon remaing directionally oriented with the surgical site of operation. Another way the automated arm (as part of the intelligent positioning system) increases accuracy is by removing the need for the surgeon to reorient himself with the space (inside the brain) when working as a result of removing their instruments and readjusting the imaging sensor which is combined manually to an adjustable arm. In addition the automated arm can also align the illumination device (connected to either the distal end, or the imaging sensor) in orientations to provide ideal lighting to the distal end of the port. In this phase the automated arm can also perform other alignment sequences required for other imaging modalities for example, stereoscopic imaging as described above for 3D imaging. The automated attainment of stereoscopic images can readily provide more information to the surgeon again increasing their accuracy during the procedure. The automated arm 102 can also provide other imaging modalities through the use of imaging probes by automated insertion into the port or automated external scanning as required by the surgeon or determined by the navigation system in combination with the intelligent positioning system.

After the bulk resection phase the surgical procedure enters the next two simultaneous phases of fine-resection (1550 and 1560). In this phase the surgeon removes the tumor from the fringes of healthy tissue, by differentitiating, using their knowledge, between the healthy and unhealthy tissue. During fine-resection the automated arm is used in a similar manner to the gross debulking phase above.

The next phase of surgery (1570) could potentially require the automated arm to deliver therapeautic agents to the surgical site to remove any remaining unhealthy tissue from the area and assure an optimal recovery. This step can be accomplished by the navigation system in combination with the intelligent positioning system and its maneuvering of the automated arm down the port to the correct site where a therapeutic distal end instrument could be used to supply the therapeutics. In addition the arm could possibly be provided the ability to maneauvre the port as required to achieve effective delivery to all sites automatically based on inputs provided by the navigation system and/or the surgeon.

The final step (1580) involves the removal of the port and closure of the wound in addition to the application of materials to assist in healing the surgical area. In this step the automated arm is used in a similar manner to the gross de-bulking step in that the automated maneuvering of the arm by the system follows the surgeons surgical tool to provide the required view.

Once the port is removed the automated arm is maneuvered in a similar manner to the incision step providing the correct view of the surgical area during the suturing of the wound.

In another embodiment the intelligent positiong system can be provided with presurgical information to improve arm function. Examples of such information are a system plan indicating the types of movements and adjustments required for each stage of surgery as well as the operating theater instruments and personnel positioning during the phases of surgery. This would streamline the surgical process by reducing the amount of manual and customized adjustments dictated by the surgeon throughout the procedure. Other information such as the unique weights of the imaging sensors can be inputted to assure a smooth movement of the arm by automatic adjustment of the motors used to run it.

Singularities

The American National Standard for Industrial Robots and Robot Systems—Safety Requirements (ANSI/RIA R15.06-1999) defines a singularity as "a condition caused by the collinear alignment of two or more robot axes resulting in unpredictable robot motion and velocities." It is most common in robot arms that utilize a "triple-roll wrist". This is a wrist about which the three axes of the wrist, controlling yaw, pitch, and roll, all pass through a common point. An example of a wrist singularity is when the path through which the robot is traveling causes the first and third axes of the robot's wrist (i.e. robot's axes 4 and 6) to line up. The second wrist axis then attempts to spin 360° in zero time to maintain the orientation of the end effector. Another common term for this singularity is a "wrist flip". The result of a singularity can be quite dramatic and can have adverse effects on the robot arm, the end effector, and the process. Some industrial robot manufacturers have attempted to side-step the situation by slightly altering the robot's path to prevent this condition. Another method is to slow the robot's travel speed, thus reducing the speed required for the wrist to make the transition. The ANSI/RIA has mandated that robot manufacturers shall make the user aware of singularities if they occur while the system is being manually manipulated.

A second type of singularity in wrist-partitioned vertically articulated six-axis robots occurs when the wrist center lies on a cylinder that is centered about axis 1 and with radius equal to the distance between axes 1 and 4. This is called a shoulder singularity. Some robot manufacturers also mention alignment singularities, where axes 1 and 6 become coincident. This is simply a sub-case of shoulder singularities. When the robot passes close to a shoulder singularity, joint 1 spins very fast.

The third and last type of singularity in wrist-partitioned vertically articulated six-axis robots occurs when the wrist's center lies in the same plane as axes 2 and 3.

Self-Collision and Singularity Motion Interlock

Having the automated arm be mobile instills another constraint on the intelligent positioning system, which is to ensure the mobile base and the automated arm are not simultaneously in motion at any given time. This is accomplished by the system by having an auto-locking mechanism which applies brakes to the arm if the wheel brakes for the mobile base are not engaged. The reasoning for this constraint is movement of the arm without a static base will result in motion of the base (basic physics). If the arm is mounted on a vertical lifting column, the lifting column adds to this constraint set: the lifting column cannot be activated if the mobile base wheels are not braked or if the arm is in motion. Similarly, the arm cannot be moved if the lifting column is active. If the mobile base wheel brakes are released, the arm and lifting column are both disabled and placed in a braked state.

Additional Mode Constraints

Consider adding—it only moves in regard to a parameter based on
  the image—for example if the percentage of the image from the bottom of the port is least a certain percentage of the total image—or some relevant parameter
  the axial alignment—for example it moves if it is off co-axial by certain degrees greater than x Closing Statements (Non-Limitations of Draft Accordingly, in some embodiments of the present disclosure, system, devices and methods are described that employ imaging devices, guidance devices, tracking devices, navigation systems, software systems and surgical tools to enable a fully integrated and minimally invasive surgical approach to performing neurological and other procedures, such as previously inoperable brain tumors, in addition to the intracranial procedure using the port based method described above. It is to be understood, however, that the application of the embodiments provided herein is not intended to be limited to neurological procedures, and may be extended to other medical procedures where it is desired to access tissue in a minimally invasive manner, without departing from the scope of the present disclosure. Non-limiting examples of other minimally invasive procedures include colon procedures, spinal, orthopedic, open, and all single-port laparoscopic surgery that require navigation of surgical tools in narrow cavities. The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

While the teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims.

What is claimed is:

1. An automated arm assembly for use during a medical procedure on an anatomical part, the automated arm assembly comprising:
    a base frame;
    a multi-joint arm operably connected to the base frame and having a distal end that is detachably connectable to an end effector;
    an optical imaging device mounted on the end effector;
    a weight operably connected to the base frame that provides a counterweight to the multi-joint arm;
    a positioning control system operably connected to the multi-joint arm and which is also connectable to a surgical navigation system which is configured to provide information relating to a position of a target, said control system configured to receive input from said surgical navigation system;
    the positioning control system configured for, based on input from said surgical navigation system:
        identifying a position and an orientation for the target in a predetermined coordinate frame with respect to the anatomical part;
        obtaining a position and an orientation of the optical imaging device mounted on the automated arm being located outside and spaced away from the anatomical part and the target, the position and orientation of the optical imaging device being defined in the predetermined coordinate frame;
        obtaining a desired standoff distance and a desired orientation between the target and the optical imaging device;
        instructing the multi-joint arm to move the optical imaging device to the desired standoff distance and desired orientation;
        upon movement of the target, determining a new desired standoff distance and a new desired orientation between the optical imaging device and the preselected portion of the target such that a preselected portion of the target is located in a field of view of the optical imaging device; and
        instructing the multi-joint arm to move the optical imaging device to the new desired standoff distance and desired orientation.

2. The automated arm assembly according to claim 1 further including a tower attached to the base frame and extending upwardly therefrom, the multi-joint arm is attached to the tower and extends outwardly therefrom.

3. The automated arm assembly according to claim 2 wherein the arm is movably upwardly and downwardly on the tower.

4. The automated arm assembly according to claim 1 further comprising a supporting beam with one end movably attached to the tower and the other end to the automated arm.

5. The automated arm assembly according to claim 1 wherein the multi-joint arm has at least six degrees of freedom.

6. The automated arm assembly according to claim 1 wherein the automated arm assembly may be moved manually.

7. The automated arm assembly according to claim 1 wherein the base frame further includes wheels.

8. The automated arm assembly according to claim 1 wherein the end effector is tracked using the detection system.

9. The automated arm assembly according to claim 1 wherein multi-joint arm further includes tracking markers which are tracked using the detection system.

10. The automated arm assembly according to claim 1 further including a radial arrangement attached to the distal end of the multi-joint arm and the end effector is movable attached to the radial arrangement whereby the end effector moves along the radial arrangement responsive to information from the control system.

11. The automated arm assembly according to claim 1 further including a joy stick operably connected to the control system and movement of the multi-joint arm is controllable by the joy stick.

12. The automated arm assembly according to claim 1 wherein the end effector is one of an external video scope, an abrasion laser, a gripper, an insertable probe or a micromanipulator.

13. The automated arm assembly according to claim 1 wherein the end effector is a first end effector and further including a second end effector attachable proximate to the distal end of the multi-joint arm.

14. The automated arm assembly according to claim 13 wherein the second end effector is wide angle camera.

15. The automated arm assembly according to claim 1 wherein the control system constrains the movement of the multi-joint arm based on defined parameters.

16. The automated arm assembly according to claim 15 wherein the defined parameters include space above patient, floor space, maintaining surgeon line of sight, maintaining tracking camera line of sight, mechanical arm singularity, self-collision avoidance, patient collision avoidance, base orientation, and a combination thereof.

17. The automated arm assembly according to claim 1 further including a protective dome attached to the multi-joint arm and the distal end of the multi-joint arm is constrained to move only within the protective dome.

18. The automated arm assembly according to claim 1 wherein a virtual safety zone is defined by the control system and the distal end of the multi-joint arm is constrained to move only within the safety zone.

19. The automated arm assembly according to claim 1 wherein the control system is configured for, upon determining a new desired standoff distance and a new desired orientation between the imaging device and the preselected portion of the target, calculating a desired focus and zoom level for the imaging device and adjusting the focus and zoom level of the imaging device to the desired focus and zoom level when the imaging device is moved to the new desired standoff distance and new orientation.

20. The automated arm assembly according to claim 19 including a visual display, and wherein the control system is configured to display an image of the preselected portion of the target at the desired focus and zoom level of the imaging device.

* * * * *